(12) United States Patent
Toyonaga et al.

(10) Patent No.: US 12,196,768 B2
(45) Date of Patent: Jan. 14, 2025

(54) METHOD OF TESTING A BLOOD FOR MACROLIDE IMMUNOSUPPRESSANT

(71) Applicant: FUJIREBIO INC., Shinjuku-ku (JP)

(72) Inventors: Masaya Toyonaga, Tokyo (JP); Yoshiyuki Hotta, Tokyo (JP)

(73) Assignee: FUJIREBIO INC., Shinjuku-ku (JP)

( * ) Notice: Subject to any disclaimer, the term of this patent is extended or adjusted under 35 U.S.C. 154(b) by 697 days.

(21) Appl. No.: 16/957,301

(22) PCT Filed: Dec. 19, 2018

(86) PCT No.: PCT/JP2018/046785
§ 371 (c)(1),
(2) Date: Jun. 23, 2020

(87) PCT Pub. No.: WO2019/131380
PCT Pub. Date: Jul. 4, 2019

(65) Prior Publication Data
US 2021/0285975 A1    Sep. 16, 2021

(30) Foreign Application Priority Data
Dec. 25, 2017 (JP) .................. 2017-248297

(51) Int. Cl.
*G01N 33/94* (2006.01)
*G01N 33/53* (2006.01)

(52) U.S. Cl.
CPC ..... *G01N 33/9493* (2013.01); *G01N 33/5308* (2013.01)

(58) Field of Classification Search
CPC ................ G01N 33/5308; G01N 33/9493
See application file for complete search history.

(56) References Cited

U.S. PATENT DOCUMENTS

| | | |
|---|---|---|
| 2006/0216762 A1 | 9/2006 | Belenky et al. |
| 2007/0087396 A1 | 4/2007 | Konrath et al. |
| 2008/0311676 A1 | 12/2008 | Brate et al. |
| 2009/0042223 A1 | 2/2009 | Wei et al. |
| 2009/0155929 A1 | 6/2009 | Wei et al. |
| 2009/0275062 A1 | 11/2009 | Konrath et al. |
| 2009/0325193 A1 | 12/2009 | Grenier et al. |
| 2009/0325197 A1 | 12/2009 | Drengler et al. |
| 2010/0297670 A1 | 11/2010 | Wei et al. |
| 2011/0287446 A1 | 11/2011 | Kanda et al. |
| 2011/0318754 A1 | 12/2011 | Wei |
| 2012/0288875 A1 | 11/2012 | Grenier et al. |
| 2016/0313310 A1 | 10/2016 | Wei et al. |
| 2017/0192024 A1* | 7/2017 | Tojo ............... B01D 15/265 |
| 2018/0024124 A1* | 1/2018 | Wu ..................... G01N 1/44 |
| | | 435/7.1 |

FOREIGN PATENT DOCUMENTS

| | | |
|---|---|---|
| EP | 2 232 264 B1 | 12/2015 |
| JP | 2008-538001 A | 10/2008 |
| JP | 2010-515064 A | 5/2010 |
| JP | 2011-506973 A | 3/2011 |
| JP | 2001-514737 A | 9/2011 |
| JP | 5124467 B2 | 11/2012 |
| JP | 5134692 B2 | 1/2013 |
| JP | 5174898 B2 | 4/2013 |
| JP | 5450092 B2 | 3/2014 |
| JP | 5690888 B2 | 3/2015 |
| JP | 2016-540220 A | 12/2016 |
| WO | WO 98/00696 A1 | 1/1998 |
| WO | WO 2009/078875 A1 | 6/2009 |
| WO | WO 2010/092958 A1 | 8/2010 |
| WO | WO 2015/178460 A1 * | 11/2015 |
| WO | WO 2016/155111 * | 10/2016 |
| WO | WO 2016/155111 A1 * | 10/2016 |

OTHER PUBLICATIONS

Extended European Search Report issued Jul. 8, 2021 in European Patent Application No. 18895443.2, 7 pages.
Adriana Mika, et al., "Current methods of the analysis of immunosuppressive agents in clinical materials: a review," Journal of Pharmaceutical and Biomedical Analysis, vol. 127, XP029602262, 2016, pp. 207-231.
International Search Report issued on Apr. 2, 2019 in PCT/JP2018/046785 filed on Dec. 19, 2018, 2 pages.

* cited by examiner

*Primary Examiner* — Galina M. Yakovleva
(74) *Attorney, Agent, or Firm* — Oblon, McClelland, Maier & Neustadt, L.L.P.

(57) ABSTRACT

The present invention provides a method of testing a blood for a macrolide immunosuppressant conveniently and/or highly accurately. Specifically, the present invention provides a method of testing a blood for a macrolide immunosuppressant, including:
(a) treating a blood sample containing a macrolide immunosuppressant or a metabolite thereof having a macrolide structure with an acid or an alkali; and
(b) measuring a concentration of the macrolide immunosuppressant or the metabolite in the blood sample by using an antibody.

2 Claims, 10 Drawing Sheets

METHOD OF TESTING A BLOOD FOR MACROLIDE IMMUNOSUPPRESSANT

TECHNICAL FIELD

The present invention relates to a method of testing a blood for a macrolide immunosuppressant, and the like.

BACKGROUND ART

Macrolide immunosuppressants including tacrolimus (FK506) and cyclosporine A are effective for avoiding a rejection after organ transplantation, as well as for treatment of an autoimmune disease and so forth. For proper treatment of these diseases, concentration of the drug in a blood is required to be maintained in a proper range for treatment, so that it is necessary to monitor the drug concentration in a blood during a treatment period.

Most of tacrolimus and cyclosporine A administered by a patient are in an erythrocyte fraction of the patient's blood. Therefore, a whole blood including the erythrocyte fraction is used as a blood sample for Therapeutic Drug Monitoring (TDM).

When the blood sample such as whole blood contains a binding protein to the drug, in order to measure the drug concentration in the blood sample, it is indispensable to dissociate the drug in the blood sample from this binding protein by means of a proper pretreatment. In such a pretreatment, a chemical substance such as an organic solvent, a denaturing agent, or a surfactant is generally used.

Examples of the prior art describing such a pretreatment include following literatures.

Patent Literature 1 describes use of an amphoteric surfactant and a saponin.

Patent Literature 2 describes use of a hemolytic agent containing a nonionic surfactant (for example, saponin) or octyl phenoxy polyethoxy ethanol, and an extracting agent consisting of a surfactant of a bile acid salt.

Patent Literature 3 describes use of a reagent including dimethyl sulfoxide (DMSO), a glycol (for example, ethylene glycol), and a zinc salt (for example, zinc sulfate).

Patent Literature 4 describes use of a protease, a glycol (for example, ethylene glycol), and an alcohol (for example, methanol).

Patent Literature 5 describes use of an extracting reagent sample including a glycol (for example, ethylene glycol), an alcohol (for example, methanol), and a salt (for example, sodium chloride).

Patent Literature 6 describes use of saponin, methanol, ethylene glycol, and zinc sulfate.

Patent Literature 7 describes use of a hemolytic agent and a surfactant [for example, an ionic surfactant (such as SDS) and a nonionic surfactant (for example, Triton™ X-405)].

Patent Literature 8 describes use of a liberating agent (for example, an analogue of a hydrophobic drug) and a selective solubilizing agent (for example, ethylene glycol, glycerol, 1-methoxy-2-propanol, dimethyl sulfoxide (DMSO), dimethyl sulfone, or dimethyl formamide).

Patent Literature 9 describes use of an extracting reagent composition including dimethyl sulfoxide (DMSO), at least one divalent metal salt, and water, the DMSO concentration in the extracting reagent composition being 50% or more by volume.

In order to separate the drug from the binding protein thereof after the drug is dissociated from the binding protein thereof, many of these pretreatments require a precipitation operation (centrifugal separation) of the protein component.

PRIOR ART REFERENCES

Patent Literatures

Patent Literature 1: Japanese laid-open Patent Publication No. 2008-538001
Patent Literature 2: Japanese Patent No. 5124467
Patent Literature 3: Japanese Patent No. 5134692
Patent Literature 4: Japanese Patent No. 5450092
Patent Literature 5: Japanese Patent No. 4968611
Patent Literature 6: Japanese Patent No. 5174898
Patent Literature 7: Japanese Patent No. 5690888
Patent Literature 8: Japanese Patent No. 4940438

SUMMARY OF INVENTION

Problem to be Solved by the Invention

In the prior arts as described above, pretreatment of the sample by a special substance and the precipitation operation are required thereby readily leading to a complicate procedure as a whole, so that there is a problem in that simplification of the assay is difficult.

In addition, in the method using an organic solvent having a high volatility, the organic solvent evaporates in the steps of extraction and at the time of incubation during assay procedure; and thus, there is a problem of poor accuracy because measurement value of the drug concentration appears to be higher than the actual value thereof.

Accordingly, the object of the present invention is to provide an alternative method with which the blood test about a macrolide immunosuppressant can be carried out conveniently and/or highly accurately.

Solution to Problem

The inventors of the present invention carried out an extensive investigation, and as a result, it was found that when the blood test about a macrolide immunosuppressant is carried out with an antibody, pretreatment of the blood sample with an acid or an alkali (base) is effective and that the above-mentioned problems could be solved with such pretreatment; and on the basis of these findings, the present invention could be completed.

Namely, the present invention is as follows.

[1] A method of testing a blood for a macrolide immunosuppressant, comprising:
  (a) treating a blood sample containing a macrolide immunosuppressant or a metabolite thereof having a macrolide structure with an acid or an alkali; and
  (b) measuring a concentration of the macrolide immunosuppressant or the metabolite in the blood sample by using an antibody.

[2] The method according to [1], wherein the macrolide immunosuppressant is tacrolimus, cyclosporine A, or everolimus.

[3] The method according to [1] or [2], wherein the blood sample is a human blood sample.

[4] The method according to any of [1] to [3], wherein the treatment of the blood sample is performed with an acid.

[5] The method according to [4], wherein the treatment with the acid is performed by mixing the blood sample with an acidic buffer.

[6] The method according to [5], wherein pH of the acidic buffer is in a range of 1.0 to 5.0.

[7] The method according to any of [1] to [6], wherein the antibody is IgG, IgM, or an antibody fragment thereof.

[8] The method according to any of [1] to [7], comprising:
(a') treating the blood sample containing the macrolide immunosuppressant or the metabolite with the acid or the alkali to form an acidic blood sample or an alkaline blood sample; and
(b') measuring the concentration of the macrolide immunosuppressant or the metabolite in the acidic blood sample or in the alkaline blood sample by using the antibody.

[9] The method according to any of [1] to [7], comprising:
(a") treating the blood sample containing the macrolide immunosuppressant or the metabolite with the acid or the alkali to form an acidic blood sample or an alkaline blood sample, and then neutralizing the acidic blood sample or the alkaline blood sample to form a neutral blood sample; and
(b") measuring the concentration of the macrolide immunosuppressant or the metabolite in the neutral blood sample by using the antibody.

[10] The method according to [9], wherein the neutralization is performed by mixing a neutralization solution containing a chaotropic denaturing agent with the acidic blood sample or with the alkaline blood sample.

[11] A reagent of testing a blood for a macrolide immunosuppressant, comprising:
(1) an acid or an alkali; and
(2) one or more antibodies to a macrolide immunosuppressant or a metabolite thereof having a macrolide structure.

[12] The reagent according to [11], wherein the acid is an acidic buffer.

[13] The reagent according to [11] or [12], wherein the reagent further comprises (3) a neutralization solution.

Effects of the Invention

According to the present invention, the blood test about a macrolide immunosuppressant can be favorably carried out.

For example, according to the present invention, the test that is convenient and highly accurate and yet has a high throughput can be achieved.

More specifically, according to the present invention, with a simple operation (pretreatment) that a blood sample containing a macrolide immunosuppressant and a metabolite thereof is made to acidic (for example, mixing of the blood sample with an acidic buffer) or made to alkaline (for example, mixing of the blood sample with an alkaline buffer), concentrations of the macrolide immunosuppressant and of the metabolite thereof in the acidic blood sample or in the alkaline blood sample can be measured very well with an antibody. Therefore, not only fluctuation of the measured value due to different technical proficiency levels of individuals can be avoided, but also a high throughput of the test can be improved.

In addition, according to the present invention, because use of an organic solvent is not indispensable, concentration due to evaporation of the organic solvent can be avoided; and thus, concentrations of the macrolide immunosuppressant and of the metabolite thereof can be measured with a high accuracy.

BRIEF DESCRIPTION OF DRAWINGS

FIG. 1-2 illustrates the immunoassay of tacrolimus that is dissociated from the tacrolimus-bound protein at different pH conditions (solid phase antibody: anti-tacrolimus antibody (mouse IgM: commercially available antibody); detection antibody: anti-tacrolimus chicken IgM).

FIG. 1-3 illustrates the immunoassay of tacrolimus that is dissociated from the tacrolimus-bound protein at different pH conditions (solid phase antibody: anti-tacrolimus antibody (mouse IgG: commercially available antibody); detection antibody: anti-tacrolimus chicken IgM).

FIG. 2 illustrates the correlation between the measured value of the tacrolimus concentration and the spike concentration of tacrolimus in the specimen when the blood sample containing tacrolimus (substance for calculation line) and the binding protein thereof is pretreated with an acid.

FIG. 3 illustrates the immunoassay of cyclosporine A that is dissociated from the cyclosporine A-bound protein at different pH conditions (solid phase antibody: anti-cyclosporine A antibody (mouse IgG: antibody of the inventors' company); detection antibody: anti-cyclosporine A chicken IgM).

FIG. 5-1 illustrates the binding rate (%) of the anti-tacrolimus antibody with the biotin-labelled tacrolimus in accordance with concentration of various tacrolimus analogous compounds in the neutral solution.

FIG. 5-2 illustrates the binding rate (%) of the anti-tacrolimus antibody with the biotin-labelled tacrolimus in accordance with concentration of various tacrolimus analogous compounds in the acidic solution.

FIG. 8-1 illustrates the immunoassay result in accordance with the tacrolimus concentration in the specimen that is obtained by treating the whole blood specimen with the neutralization solution containing urea after treating this whole blood specimen with an acid.

FIG. 8-2 illustrates the immunoassay result in accordance with the tacrolimus concentration in the specimen that is obtained by treating the whole blood specimen with the neutralization solution containing guanidine hydrochloride after treating this whole blood specimen with an acid.

EMBODIMENTS FOR CARRYING OUT THE INVENTION

Figure 1:
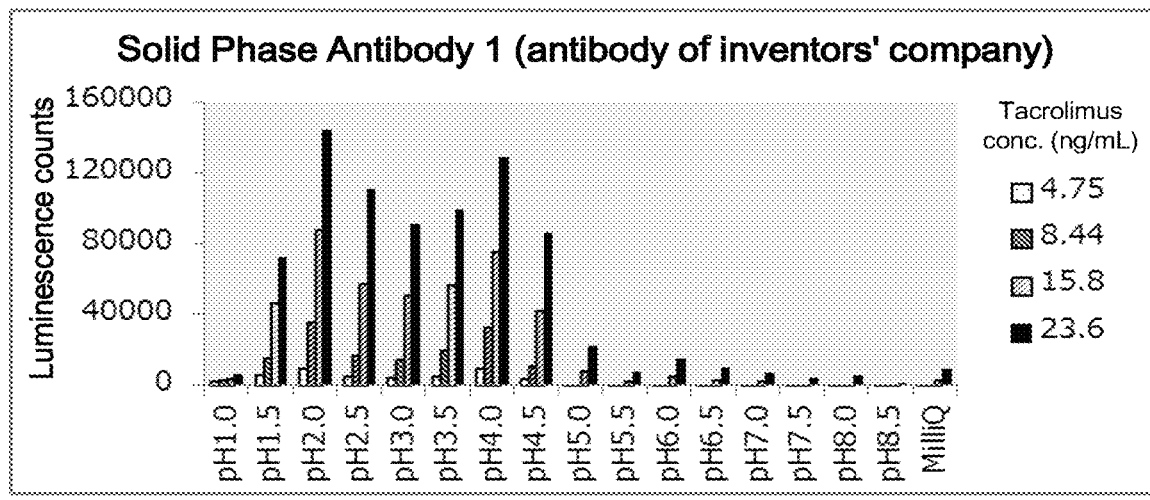
FIG. 1-1 illustrates the immunoassay of tacrolimus that is dissociated from the tacrolimus-bound protein at different pH conditions (solid phase antibody: anti-tacrolimus antibody (mouse IgG: antibody of the inventors' company); detection antibody: anti-tacrolimus chicken IgM).

The present invention provides a method of testing a blood for a macrolide immunosuppressant, comprising:
  (a) treating a blood sample containing a macrolide immunosuppressant or a metabolite thereof having a macrolide structure with an acid or an alkali; and
  (b) measuring a concentration of the macrolide immunosuppressant or the metabolite in the blood sample by using an antibody.

The blood sample to be used in the present invention is an animal blood sample containing a macrolide immunosuppressant or a metabolite thereof having a macrolide structure. Such a blood sample can be taken from an animal that is administered with the macrolide immunosuppressant. The animal blood sample contains a binding protein to the macrolide immunosuppressant or to the metabolite thereof having a macrolide structure, in which the macrolide immunosuppressant or the metabolite thereof having a macrolide structure, and the binding protein are bound to each other so that they can form a complex thereof. The animals from which such a blood sample is derived are preferably mammals (for example, primates such as human, monkey, and chimpanzee; rodents such as mouse, rat, and rabbit; and domestic animals and working animals such as cow, pig, horse, goat, and sheep), more preferably primates, still more preferably human. Examples of the blood sample include a whole blood, a serum, a plasma, and other blood fractions. Most of the macrolide immunosuppressant or the metabolite thereof having a macrolide structure, and of the binding protein to them are present in a certain blood fraction (for example, an erythrocyte fraction), so that such a blood fraction or a blood sample containing this blood fraction (for example, a whole blood) may be used in measurement of concentration of the macrolide immunosuppressant or the metabolite thereof having a macrolide structure in the blood. In view of simple measurement of the concentration with omitting a fractionation operation, use of a whole blood is preferable as the blood sample. In addition, it is preferable that the blood sample be taken from a mammal suffered from a disease requiring immune suppression (for example, autoimmune disease, rheumatoid arthritis, myasthenia gravis, Crohn's disease, lupus nephritis, active ulcerative colitis, polymyositis, graft versus host disease (GVDH), and dermatomyositis-associated interstitial pneumonia), or from a mammal transplanted with an organ, a tissue, or a cell (for example, heart transplant, kidney transplant, bone marrow transplant, lung transplant, lever transplant, pancreas transplant, and small intestine transplant). The blood sample taken from these mammals may be subjected to pretreatment (for example, filtration, heating, and hemolysis).

The macrolide immunosuppressant is a compound that includes a macrolide structure (cyclic lactone structure composed of 12 or more atoms) and has an activity to lower or inhibit an activity of an immune system. Examples of the macrolide immunosuppressant include tacrolimus (FK506), cyclosporine A, sirolimus (rapamycin), and derivatives of them (for example, everolimus and temsirolimus), as well as zotarolimus, biolimus, novolimus, pimecrolimus, myolimus, myolimus, and deforolimus.

The metabolite of the macrolide immunosuppressant having a macrolide structure is different depending on kind of the macrolide immunosuppressant, and thus not particularly limited as long as this can be bound to a binding protein in accordance with the kind of the macrolide immunosuppressant. It is reported that in the case that the macrolide immunosuppressant is tacrolimus, Examples of the tacrolimus metabolite having the macrolide structure include 13-O-desmethyl tacrolimus (MI), 31-O-desmethyl tacrolimus (MII), 15-O-desmethyl tacrolimus (MIII), 12-O-hydroxyl tacrolimus (MIV), 15,31-O-didesmethyl tacrolimus (MV), 13,31-O-didesmethyl tacrolimus (MVI), 13,15-O-didesmethyl tacrolimus (MVII), VIII tacrolimus, C22 oxime tacrolimus, C24 succinate tacrolimus, and C32 succinate tacrolimus (Clin. Chem., 2014 April, 60(4), 621-630), and that such tacrolimus metabolites can be bound to a tacrolimus-binding protein to form respective complexes (Ther. Drug. Monit., 1999 June, 21(3), 274-280; Biochem. Biophys. Res. Commun., 1994 July, 15, 202(1), 437-443; and Drug Metabolism and Disposition, November 1993, 21(6), 971-977). It is reported that in the case that the macrolide immunosuppressant is cyclosporine A, Examples of the cyclosporine A metabolite having the macrolide structure include cyclosporine AM1, cyclosporine AM9, cyclosporine AM4N, cyclosporine AM1c, and cyclosporine AM19 (Br. J. Clin. Pharmacol., 2003 February, 55(2), 203-211), and that such cyclosporine A metabolites can be bound to a cyclosporine A-binding protein to form respective complexes (Clin. Biochem., 1991 February, 24(1), 71-74; CLIN. CHEM., 37(3), 403-410 (1991)). It is reported that Examples of the sirolimus metabolite having the macrolide structure include 16-O-demethyl sirolimus, 24-hydroxy sirolimus, 25-hydroxy sirolimus, 46-hydroxy sirolimus, 39-O-demethyl sirolimus, 7-O-demethyl sirolimus, 32-O-demethyl sirolimus, 41-O-demethyl sirolimus, hydroxy sirolimus, seco-sirolimus, 11-hydroxy sirolimus, 3,4-dihydrodiol sirolimus, and 5,6-dihydrodiol sirolimus (Ther. Drug. Monit., 2015, June, 37(3), 395-399; the material attached to the application form for manufacturing and sales of Rapalimus 1 mg, Part 2 (module 2), 2.4 General Assessment of Non-clinical Test), and that such sirolimus metabolites can be bound to a sirolimus-binding protein to form respective complexes (Clin. Biochem., 1996 August, 29(4), 309-313). Examples of the everolimus metabolite having the macrolide structure include 46-hydroxy everolimus, 24-hydroxy everolimus, 25-hydroxy everolimus, 45-hydroxy everolimus, 2-hydroxy everolimus, 11-hydroxy everolimus, 14-hydroxy everolimus, 39-O-desmethyl everolimus, 27-O-desmethyl everolimus, and 40-O-desethyl hydroxy everolimus (sirolimus) (Ther. Drug Monit., 2007 December, 29(6), 743-749). The macrolide immunosuppressant and the metabolite of the macrolide immunosuppressant having a macrolide structure can exist at a certain ratio in the blood of animals including human, though it is necessary to take a factor such as individual difference into account. Therefore, the blood test for the macrolide immunosuppressant may also be carried out indirectly by measurement of the metabolite concentration in the blood sample. Preferably, the blood test can be carried out by measuring concentration of the macrolide immunosuppressant.

As to the binding proteins to the macrolide immunosuppressant or to the metabolite thereof having the macrolide structure included in the blood sample, various proteins that are endogenous to mammals including human are known.

More specifically, Examples of the specific binding protein to tacrolimus (FK506) or to the metabolite thereof having the macrolide structure include FK506-binding proteins (FKBPs) (for example, FKBP12, FKBP13, FKBP14, FKBP2, and FKBP3). Examples of the specific binding protein to cyclosporine A or to the metabolite thereof having the macrolide structure include cyclophilin A and cyclophilin B. Examples of the specific binding protein to sirolimus (rapamycin) and derivatives thereof or to the metabolite thereof having the macrolide structure include FKBP12. These specific binding proteins exist mainly in the erythrocyte fraction. Examples of the non-specific protein to the macrolide immunosuppressant or to the metabolite thereof having the macrolide structure include albumin, lipoprotein, and a1-acidic glycoprotein.

Any acid capable of acidifying the blood sample can be used as the acid to be used in the method of the present invention. Examples of such an acid include inorganic acids (for example, phosphoric acid, boric acid, carbonic acid, hydrochloric acid, sulfuric acid, and nitric acid), organic acids (for example, acetic acid, citric acid, glycine, tartaric acid, 2-morpholino ethane sulfonic acid (MES), formic acid, oxalic acid, lactic acid, maleic acid, trifluoroacetic acid, and phthalic acid), and a mixture of two or more (for example, two, three, four, or five) of them.

Any alkali capable of alkalizing the blood sample can be used as the alkali to be used in the method of the present invention. Examples of such an alkali include inorganic bases (for example, hydroxides of metals (for example, monovalent metals and divalent metals) such as sodium hydroxide, potassium hydroxide, magnesium hydroxide, and calcium hydroxide); hydrogen carbonate of metals (for example, monovalent metals and divalent metals) such as sodium hydrogen carbonate, potassium hydrogen carbonate, and calcium hydrogen carbonate; carbonate of metals (for example, monovalent metals and divalent metals) such as sodium carbonate, potassium carbonate, and calcium carbonate; phosphate of metals (for example, monovalent metals) such as sodium phosphate and potassium phosphate; borate of metals (for example, monovalent metals) such as sodium borate and potassium borate; and ammonia; organic bases (for example, amines such as trimethyl amine and triethyl amine; and nitrogen-containing heterocyclic compounds such as pyridine); and a mixture of two or more (for example, two, three, four, or five) of them.

In the present invention, any of an acid and an alkali can be used in the treatment of the blood sample. In view of the detection sensitivity of the macrolide immunosuppressant in the blood sample, it is preferable that the blood sample be treated with an acid. Hereinafter, the treatment with an acid or an alkali will be explained in detail.

The treatment of the blood sample containing the macrolide immunosuppressant or the metabolite thereof having the macrolide structure with an acid or an alkali is not particularly limited as long as the treatment can increase acidity (in other words, lower the pH value) or basicity (in other words, raise the pH value) of the blood sample to the degree that the macrolide immunosuppressant or the metabolite thereof having the macrolide structure can be dissociated from the binding protein to them. Examples of the treatment include mixing of the blood sample (in other words, dilution of the blood sample) with an acidic solution (for example, an acidic buffer or an acidic solution not having a buffering capacity) or an alkaline solution (for example, an alkaline buffer or an alkaline solution not having a buffering capacity), and dissolution of an acid (solid) or an alkali (solid) into the blood sample. In view of simple operation and the like, mixing of the blood sample with an acidic solution or an alkaline solution is preferable.

Volume of the blood sample to be treated is not particularly limited as long as the macrolide immunosuppressant or the metabolite thereof having the macrolide structure can be measured with the method of the present invention. The volume is in the range of, for example, 0.1 to 500 µL, preferably 0.5 to 400 µL, more preferably 1.0 to 300 µL, still more preferably 2.0 to 200 µL. Volume of the acidic solution or of the alkaline solution to be mixed with the blood sample is not particularly limited as long as the acidity or the alkalinity of the blood sample can be increased to the degree that the macrolide immunosuppressant or the metabolite thereof having the macrolide structure can be dissociated from the binding protein to them. The volume thereof is in the range of, for example, 0.5 to 5,000 µL, preferably 1.0 to 3,000 µL, more preferably 2.0 to 1,000 µL, still more preferably 5.0 to 500 µL. Mixing ratio of the blood sample to the acidic solution or to the alkaline solution (blood sample/acidic solution or blood sample/alkaline solution) is not particularly limited as long as the acidity or the alkalinity of the blood sample can be increased. The mixing ratio is in the range of, for example, 1/100 to 100, preferably 1/50 to 50, more preferably 1/30 to 30, still more preferably 1/20 to 20. The blood sample is derived from the animals as mentioned above; and this has a neutral nature. When such a blood sample is treated with an acid, the macrolide immunosuppressant or the metabolite thereof having the macrolide structure included in the blood sample can be dissociated from the binding protein to them. Therefore, with such a treatment, the acidic blood sample or the alkaline blood sample containing the macrolide immunosuppressant or the metabolite thereof having the macrolide structure, which is in the dissociated state from the binding protein, can be prepared. In order to sufficiently dissociate the macrolide immunosuppressant or the metabolite thereof having the macrolide structure from the binding protein, after mixing or dissolution, it is preferable that a time sufficient for the dissociation be set (for example, allowed to be stand) in a certain temperature condition. On the other hand, in order to avoid hydrolysis of the components (for example, the macrolide immunosuppressant or the metabolite thereof having the macrolide structure) by the acid as much as possible, it is preferable that the temperature be not too high and that the period be not too long. Therefore, such temperature is, for example, 5 to 45° C., preferably 15 to 40° C. Such period is in the range of, for example, 10 seconds to 60 minutes, preferably 20 seconds to 30 minutes, more preferably 30 seconds to 15 minutes.

In view of simple and rapid preparation of the acidic blood sample as well as in view of affording a constant acidity to the acidic blood sample and the like, treatment of the blood sample in the acidic solution is preferably effected by mixing of the blood sample with an acidic buffer. The buffer containing any acid capable of exhibiting a buffering capacity in an acidic region may be used as the acidic buffer. Examples of such an acid include inorganic acids (for example, phosphoric acid, boric acid, and carbonic acid), organic acids (for example, acetic acid, citric acid, glycine, tartaric acid, 2-morpholino ethane sulfonic acid (MES), trifluoroacetic acid, and phthalic acid), and a mixture of two or more (for example, two, three, four, or five) of them.

The pH of the acid solution such as the acidic buffer can be changed depending on the factors such as kind and concentration of the macrolide immunosuppressant or the metabolite thereof having the macrolide structure and the binding protein to them, and is in the range of, for example, 1.0 to 5.0. As the acidic solution of pH 1.0 to 5.0, the buffer capable of exhibiting the buffering capacity in this acidic region is preferable. Examples of such a buffer include a phosphate buffer, a tartrate buffer, a citrate buffer, an acetate buffer, a trifluoroacetate buffer, a phthalate buffer, a glycine buffer, a carbonate-hydrogen carbonate buffer, and a 2-morpholino ethane sulfonate (MES) buffer. In order to remove the effects of the factors mentioned above as much as possible thereby enhancing the versatility thereof or the like, pH may be preferably 1.5 or higher, more preferably 2.0 or higher, still more preferably even 2.5 or higher; and pH may be preferably 4.8 or lower, more preferably even 4.5 or lower. More specifically, pH may be preferably in the range of 1.5 to 4.8, more preferably 2.0 to 4.8, still more preferably of 2.5 to 4.8, particularly preferably 2.5 to 4.5. Measurement of pH may be carried out by using known methods in the art. Preferably, pH that is measured by using a pH meter having a glass electrode at 25° C. may be used.

In view of simple and rapid preparation of the alkaline blood sample as well as in view of affording a constant alkalinity to the alkaline blood sample, and the like, treatment of the blood sample in the alkaline solution is preferably effected out by mixing of the blood sample with an alkaline buffer. The buffer containing any base capable of exhibiting a buffering capacity in a basic region may be used as the alkaline buffer. Such bases are the same as those described above.

The pH of the alkaline solution such as the alkaline buffer can be changed depending on the factors such as kind and concentration of the macrolide immunosuppressant or the metabolite thereof having the macrolide structure as well as on the binding protein to them, and is in the range of, for example, 8.0 to 13.0. As the alkaline solution of pH 8.0 to 13.0, the buffer capable of exhibiting the buffering capacity in this basic region is preferable. Examples of such buffer include a phosphate buffer, a carbonate-hydrogen carbonate buffer, a borate buffer, an MES buffer, an N-(2-acetamide) imino diacetate (ADA) buffer, piperazine-1,4-bis(2-ethanesulfonate) (PIPES) buffer, an N-(2-acetamide)-2-aminoethane sulfonate (ACES) buffer, a calamine hydrochloride buffer, an N,N-bis(2-hydroxyethyl)-2-aminoethane sulfonate (BES) buffer, an N-tris(hydroxymethyl)methyl-2-aminoethane sulfonate (TES) buffer, a 2-[4-(2-hydroxyethyl)-1-piperazinyl]ethane sulfonate (HEPES) buffer, an acetamide glycine buffer, a tricine buffer, a glycinamide buffer, a bicine buffer, and a tris buffer. In order to remove the effects of the factors mentioned above as much as possible thereby enhancing the versatility thereof or the like, pH may be preferably 9.0 or higher; and pH may be preferably 12.0 or lower, particularly preferably 11.0 or lower. More specifically, pH may be in the range of preferably 9.0 to 12.0, particularly preferably in the range of 9.0 to 11.0. Measurement of pH may be carried out in the same way as mentioned above.

The acidic solution such as the acidic buffer or the alkaline solution such as the alkaline buffer may contain or may not contain an antibody to the macrolide immunosuppressant or to the metabolite thereof having the macrolide structure. In the case that the acidic solution or the alkaline solution contains such an antibody, concentration of the macrolide immunosuppressant or the metabolite thereof having the macrolide structure may be measured by using this antibody. The acidic solution or the alkaline solution may further contain other substances. Examples of the other substance include water-miscible organic solvents (for example, an alcohol, an ether, and an ester), denaturing agents (for example, a chaotropic agent), surfactants (for example, a cationic surfactant, an anionic surfactant, an amphoteric surfactant, a non-ionic surfactant, and a bile acid salt surfactants), hemolytic agents, and competitive agents (for example, an analogous compound) (for example, Patent Literatures 1 to 9 mentioned above).

The values of pH of the acidic blood sample or of the alkaline blood sample, prepared by treating the blood sample with an acid or with an alkali, are the same as the above-mentioned pH of the acidic solution such as the acidic buffer or the alkaline solution such as the alkaline buffer. Therefore, examples and preferable examples of pH of the acidic blood sample or of the alkaline blood sample may be referred to those of the acidic solution or of the alkaline solution.

The antibody to be used in the present invention is an antibody to the macrolide immunosuppressant or to the metabolite thereof having the macrolide structure. Such an antibody may be any of a polyclonal antibody and a monoclonal antibody. The antibody may be any isotype of immunoglobulin (for example, IgG, IgM, IgA, IgD, IgE, and IgY). The antibody may also be a full length antibody. The full length antibody means the antibody that includes a heavy chain and a light chain, each including a variable region and a constant region (for example, an antibody including two Fab portion and an Fc portion). The antibody may also be an antibody fragment derived from the full length antibody. The antibody fragment is a part of the full length antibody; Examples thereof include constant region deleted antibodies (for example, F(ab')$_2$, Fab', Fab, and Fv). The antibody may also be a modified antibody such as a single chain antibody. Preferably, the antibody may be IgG or IgM, or antibody fragments thereof. The present invention can use not only one antibody but also two or more of them (for example, two or three).

The antibody that can recognize only the macrolide immunosuppressant or the metabolite thereof having the macrolide structure can be used as the antibody. In the case that two or more antibodies are used in the present invention, in addition to the antibody that can recognize only the macrolide immunosuppressant or the metabolite thereof having the macrolide structure, an antibody that can recognize a complex comprising the macrolide immunosuppressant or the metabolite thereof having the macrolide structure and an antibody to them, can be used as the antibody to the macrolide immunosuppressant or to the metabolite thereof having the macrolide structure (for example, WO2004/11644; WO2013/042426; and Nucleic Acids Res. (February 2011), vol. 39, No. 3, e14).

The antibody to the macrolide immunosuppressant or to the metabolite thereof having the macrolide structure can be prepared by using an any method known in the art. For example, the antibody can be prepared by using, as an antigen, the macrolide immunosuppressant or the metabolite thereof having the macrolide structure. Because antibodies to the macrolide immunosuppressant or to the metabolite thereof having the macrolide structure are commercially available, these commercially available antibodies can also be used.

In the present invention, one or more of the antibody (for example, one or two) to the macrolide immunosuppressant or to the metabolite thereof having the macrolide structure can be used. In the present invention, a secondary antibody to the antibody can also be used.

The antibody may be immobilized to a solid phase. As used herein, the antibody immobilized on a solid phase is sometimes simply called a solid phase antibody. Examples of the solid phase include a solid phase capable of accommodating or mounting a liquid phase therein or thereon (for example, containers such as a well plate, a microchannel, a glass capillary, a nano-pillar, a monolith column, and a tube; and supports such as a plate, a membrane, and a filter paper), and a solid phase capable of being suspended or dispersed in a liquid phase (for example, a solid phase carriers such as particle). Examples of the material of the solid phase include glass, plastics, metal, and carbon. A non-magnetic material or a magnetic material may be used as the material of the solid phase. In view of convenience in the operation or the like, a magnetic material is preferable as the solid phase supporting material. Any method known in the art can be used as the method to immobilize the antibody on the solid phase. Examples of such a method include a physical adsorption method, a covalent bonding method, a method using an affinity substance (for example, biotin and streptavidin), and an ionic binding method.

The antibody may be labeled with a labeling substance. As used herein, the antibody labeled with a labeling substance is sometimes simply called a labeled antibody. Examples of the labeling substance include enzymes (for example, peroxidase, alkaline phosphatase, luciferase, and β-galactosidase), affinity substances (for example, streptavidin and biotin), fluorescent substances or proteins (for example, fluorescein, fluorescein isothiocyanate, rhodamine, green fluorescent protein, and red fluorescent protein), luminescence or absorption substances (for example, luciferin, aequorin, and acridinium), and radioactive substances (for example, $^3H$, $^{14}C$, $^{32}P$, $^{35}S$, and $^{125}I$).

Measurement of the concentration of the macrolide immunosuppressant or the metabolite thereof having the macrolide structure with an antibody can be carried out by an immunoassay method. Examples of the immunoassay method include enzyme immunoassay (EIA) [for example, a chemiluminescence EIA (CLEIA) method and an enzyme adsorbent EIA (ELISA)], a fluorescence immunoassay, a chemiluminescence immunoassay, an electrochemiluminescence immunoassay, an agglomeration, an immunostaining, a flowmetry method, a biolayer interference method, an in situ PLA method, a chemical amplification type luminescence proximity homogeneous assay, a line blotting method, and a western blotting method.

The present invention is carried out by the method comprising:
(a) treating a blood sample containing a macrolide immunosuppressant or a metabolite thereof having a macrolide structure with an acid or with an alkali; and
(b) measuring a concentration of the macrolide immunosuppressant or the metabolite having the macrolide structure in the blood sample by using an antibody.

The process (a) and the process (b) may be carried out in parallel or separately. For example, When an acidic buffer or an alkaline buffer each containing the antibody to the macrolide immunosuppressant or to the metabolite thereof having the macrolide structure is used in the treatment of the blood sample with an acid or an alkali, the treatment of the blood sample with an acid or an alkali and the measurement by using the antibody can be carried out in parallel. In this case, in the measurement of the concentration with the antibody, a secondary antibody (for example, a labelled antibody) to the macrolide immunosuppressant or to the metabolite thereof having the macrolide structure may be further used, the secondary antibody being different from a first antibody (for example, a solid phase antibody) to the macrolide immunosuppressant or to the metabolite thereof having the macrolide structure contained in the acidic buffer or in the alkaline buffer. On the other hand, for example, when an acidic buffer or an alkaline buffer each containing the antibody to the macrolide immunosuppressant or to the metabolite thereof having the macrolide structure is not used in the treatment of the blood sample with an acid or with an alkali, the treatment of the blood sample with an acid or an alkali and the measurement of the concentration with the antibody can be carried out separately. In this case, the process (a) and the process (b) can be carried out continuously or discontinuously. When the process (a) and the process (b) are carried discontinuously, the blood sample treated with an acid may be subjected to further treatment. Examples of such a treatment include the same treatment as those of above-mentioned pretreatment (for example, filtration, heating, and hemolysis), change of pH, and treatment with a certain chemical substance.

In a certain embodiment, the present invention may also be carried out by the method comprising:
(a') treating the blood sample containing the macrolide immunosuppressant or the metabolite with the acid or the alkali to form an acidic blood sample or an alkaline blood sample; and
(b') measuring the concentration of the macrolide immunosuppressant or the metabolite in the acidic blood sample or in the alkaline blood sample by using the antibody.

The process (a') and the process (b') may be carried out in parallel or separately. In addition, the process (a') and the process (b') can be carried out continuously or discontinuously. For example, when the process (a') and the process (b') are carried out continuously, the acidic blood sample or the alkaline blood sample prepared in the process (a') can be subjected to the process (b') as it is. When the process (a') and the process (b') are carried out discontinuously, the acidic blood sample or the alkaline blood sample may be subjected to further treatments. Such treatments are the same as, for example, those explained with regard to the process (a) and the process (b).

The present invention is based on the findings that in the blood sample under an acidic condition or an alkaline condition, with dissociating the binding between a macrolide substance used as the immunosuppressant and a binding protein to it, not only concentration of the dissociated macrolide substance could be measured with an antibody but also quantitativity in the measurement thereof was superior. Such a macrolide substance has a specific ring structure (this has a relatively rigid structure thereby lacking flexibility), and also this is a compound having a relatively high hydrophobicity as well as a high molecular weight (molecular weight of about 800 to about 1300). As one reason for a superior quantitativity of the present invention in spite that the measurement is carried out under a relatively severe condition of an acidic condition or of an alkaline condition, there is a possibility that this superiority be derived from the use of the macrolide substance having the characteristics as mentioned above, although this explanation does not intend to limit the scope of the present invention.

In other embodiment, the present invention may also be carried out by the method comprising:
(a") treating the blood sample containing the macrolide immunosuppressant or the metabolite with the acid or the alkali to form an acidic blood sample or an alkaline blood sample, and then neutralizing the acidic blood sample or the alkaline blood sample to form a neutral blood sample; and (b") measuring the concentration of the macrolide immunosuppressant or the metabolite in the neutral blood sample by using the antibody.

Namely, in the method of the present invention, after the blood sample is treated with an acid or with an alkali, a neutralization treatment may be carried out. By the neutralization treatment, an antibody having a low resistance to an acid or an alkali can be selected as the antibody to be used in the process (process (b")) to measure the concentration of the macrolide immunosuppressant or the like by using an antibody in the later stage.

The neutralization solution to be used in the neutralization treatment is not particularly limited as long as the composition thereof can bring pH of the acidic blood sample or of the alkaline blood sample, obtained by the treatment with an acid or with an alkali, into the range of about 6.5 to about 7.5. The neutralization solution to the acidic blood sample contains, for example, the substances described as the above-mentioned alkali; and the neutralization solution having pH in the range of 8.0 to 13.0 can be suitably used. The neutralization solution to the alkaline blood sample contains, for example, the substances described as the above-mentioned acid; and the neutralization solution having pH in the range of 1.0 to 6.5 can be suitably used.

In addition, the neutralization solution may contain a chaotropic denaturing agent besides the alkaline substance or the acidic substance. Examples of the chaotropic denaturing agent include urea, thiourea, guanidine hydrochloride, guanidine thiocyanate, sodium salicylate, sodium thiocyanate, sodium perchlorate, acetamide, and formamide. It is preferable that the final concentration of the chaotropic denaturing agent be in the range of 0.5 to 8.0 M.

When neutralization is carried out after the blood sample is treated with an acid or with an alkali, a risk of decrease in the activity of the antibody having a low resistance to an acid or to an alkali can be reduced. On the other hand, there may be a concerned risk of decrease in the sensitivity thereof due to rebinding of the dissociated macrolide immunosuppressant with a binding protein thereof. By addition of the chaotropic denaturing agent to the neutralization solution, the influence on the rebinding can be reduced. The chaotropic denaturing agent may also be added to an acidic solution or into an alkaline solution, not into the neutralization solution as described above. Alternatively, the chaotropic denaturing agent may be added to both the neutralization solution and the acidic solution or both the neutralization solution and the alkaline solution.

The present invention also provides a reagent of testing a blood for the macrolide immunosuppressant, comprising (1) an acid or an alkali, and (2) one or more antibodies to a macrolide immunosuppressant or a metabolite thereof having a macrolide structure.

The acid and the alkali are the same as those described above. The acid or the alkali may be any of a solid and a liquid, and a liquid is preferable. Therefore, the reagent of the present invention preferably contain (1') an acidic solution or an alkaline solution, and (2') one or more antibodies (for example, one or two) to the macrolide immunosuppressant or to the metabolite thereof having a macrolide structure. The acidic solution or the alkaline solution, and pH of them are the same as those described above.

The acidic solution or the alkaline solution may be an acidic buffer or an alkaline buffer, or an acidic solution or an alkaline solution not having a buffering capacity, and it is preferably an acidic buffer or an alkaline buffer. Therefore, the reagent of the present preferably contain (1") an acidic buffer or an alkaline buffer, and (2") one or more antibodies to the macrolide immunosuppressant or the metabolite thereof having a macrolide structure. The acidic buffer or the alkaline buffer, and pH of them are as same as those described above.

The acidic solution such as the acidic buffer or the alkaline solution such as the alkaline buffer can be supplied in a liquid form or in a frozen form thereof. The acidic buffer or the alkaline buffer may be stored in the containers as described above or in a large container such as a bottle. The one or more antibodies to the macrolide immunosuppressant or to the metabolite thereof having the macrolide structure may be supplied in the dissolved form in a liquid such as a buffer, or in the frozen form thereof, or in the freeze dried form of the antibody. The one or more antibodies to the macrolide immunosuppressant or the metabolite thereof having the macrolide structure may be supplied in the free form (for example, a solution form or a frozen form) or in the immobilized form on a solid phase as described above.

In one embodiment, the reagent of the present invention may be the acidic buffer or the alkaline buffer containing the one or more antibodies to the macrolide immunosuppressant or the metabolite thereof having the macrolide structure, namely, a composition integrating (1") the acidic buffer or the alkaline buffer and (2") the one or more antibodies to the macrolide immunosuppressant or to the metabolite thereof having the macrolide structure. When the acidic buffer or the alkaline buffer as mentioned above is used, dissociation of the macrolide immunosuppressant or the metabolite thereof having the macrolide structure from the binding protein thereof by means of an acid or an alkali, and measurement of the concentration of the macrolide immunosuppressant or the metabolite thereof having the macrolide structure thus dissociated may be conveniently carried out in parallel. In this case, in addition to the acidic buffer or the alkaline buffer containing the one or more antibodies to the macrolide immunosuppressant or to the metabolite thereof having the macrolide structure, the reagent of the present invention may contain one or more antibodies to the macrolide immunosuppressant or to the metabolite thereof having the macrolide structure, these antibodies being different from the above-mentioned antibodies, and/or a secondary antibody to the antibody. Such a regent can be suitably used in the immunoassay using two or more antibodies.

In other embodiment, the reagent of the present invention may be a kit containing (1") the acidic buffer or the alkaline buffer and (2") the one or more antibodies to the macrolide immunosuppressant or the metabolite thereof having the macrolide structure in the separate form. In such a form, because the one or more antibodies to the macrolide immunosuppressant or the metabolite thereof having the macrolide structure are separated from the acidic buffer or the alkaline buffer, performance of the one or more antibodies to the macrolide immunosuppressant or the metabolite thereof having the macrolide structure can be maintained for a long period of time. In this case, the reagent of the present invention is superior in the storage property.

Furthermore, in other embodiment, the reagent of the present invention contains (3) a neutralization solution in addition to (1) an acid or an alkali and (2) one or more antibodies to a macrolide immunosuppressant or to a metabolite thereof having a macrolide structure. The neutralization solution and pH thereof are the same as those described above.

The reagent of the present invention may also contain the macrolide immunosuppressant or the metabolite thereof having the macrolide structure (standards). The macrolide immunosuppressant or the metabolite thereof having the macrolide structure can be used, for example, as a positive control and/or for preparation of a calibration curve for quantification.

The reagent of the present invention may further contain component elements necessary for the immunoassay using the antibody to the macrolide immunosuppressant or the metabolite thereof having the macrolide structure. Examples of such a component element include the labeled substance as described above, a substrate of an enzyme, a diluted solution, a secondary antibody, an antibody stabilizer, and equipment to take a sample from a mammal (for example, a syringe and a biopsy needle).

EXAMPLES

Hereinafter, the present invention will be explained by Examples in more detail, although the present invention is not limited to these Examples.

Example 1: ELISA of Detecting Tacrolimus in Whole Blood Specimen by Acid Treatment The materials used in Example 1 are as follows.
Immunoplate with 96 wells: Nunc Maxisorp C96 Immunoplate (Thermo, Catalog No.: 430341)
Anti-tacrolimus solid phase antibody 1 (mouse IgG): Tac 5-26-8 (antibody of the inventors' company)
Anti-tacrolimus solid phase antibody 2 (mouse IgM): FK1 (HyTest, Catalog No.: 4FK42)
Anti-tacrolimus solid phase antibody 3 (mouse IgG): FK2 (Biorbyt, Catalog No.: orb 79532)
Washing solution: 0.5% by volume Tween®20/PBS
Blocking solution: 1% by weight BSA/PBS
Specimen: Lyphocheck (registered trade mark) Whole Blood Immunosuppressant Control (Bio-Rad, Inc.) with Levels 1, 2, 3, 4, and 5. In this specimen, tacrolimus, cyclosporine A, and everolimus are spiked in the whole blood sample, and measurement values in various measurement systems are disclosed. The measurement values of tacrolimus by means of HPLC-MS used in this Example are 4.75 ng/ml (Level 1), 8.44 ng/ml (Level 3), 15.8 ng/ml (Level 4), and 23.6 ng/ml (Level 5). The measured values of cyclosporine A by means of HPLC-MS used in this Example are 87 ng/ml (Level 1), 152 ng/mL (Level 2), 354 ng/ml (Level 3), 755 ng/ml (Level 4), and 1211 ng/ml (Level 5). In the following Examples, concentration and number of the specimen were arbitrarily changed as needed in accordance with the assay purpose.
Culture supernatant containing the anti-tacrolimus antibody (detection antibody): CHO culture supernatant containing the anti-tacrolimus chicken IgM (antibody of the inventors' company)
Diluted solution for the culture supernatant: 1% by weight BSA/PBS
ALP-labeled antibody: alkaline phosphatase-labelled mouse anti-chicken IgM mAb (antibody of the inventors' company)
Diluted solution for the labelled antibody: 1% by weight BSA/PBS
Luminescent substrate solution: luminescent substrate for lumipulse (AMPPD)

In Example 1, following acidic buffers were used.
The phosphate buffer (pH 1.0 to pH 3.0) was prepared by mixing phosphoric acid ($H_3PO_4$) with an aqueous solution of sodium dihydrogen phosphate dihydride ($NaH_2PO_4 \cdot 2H_2O$).

The citrate buffer (pH 3.5) was prepared by mixing an aqueous solution of citric acid ($C_6H_9O_7$) with an aqueous solution of sodium citrate ($Na_3C_6H_9O_7$).

As to the acetate buffer (pH 4.0 to pH 5.5), a commercially available buffer for Biacore was used.

The phosphate buffer (pH 6.0 to pH 8.0) was prepared by mixing sodium dihydrogen phosphate dihydride ($NaH_2PO_4 \cdot 2H_2O$) with an aqueous solution of disodium hydrogen phosphate twelve hydride ($Na_2HPO_4 \cdot 12H_2O$).

As to the borate buffer (pH 8.5), a commercially available buffer for Biacore was used.

Namely, the kind and pH of the acidic buffers used in Example 1 are as follows.

TABLE 1

| Kind and pH of the acidic buffers | |
|---|---|
| pH | Kind |
| 1.0 | 100 mM phosphate buffer |
| 1.5 | 100 mM phosphate buffer |
| 2.0 | 100 mM phosphate buffer |
| 2.5 | 100 mM phosphate buffer |
| 3.0 | 100 mM phosphate buffer |
| 3.5 | 100 mM citrate buffer |
| 4.0 | 10 mM acetate buffer |
| 4.5 | 10 mM acetate buffer |
| 5.0 | 10 mM acetate buffer |
| 5.5 | 10 mM acetate buffer |
| 6.0 | 100 mM phosphate buffer |
| 6.5 | 100 mM phosphate buffer |
| 7.0 | 100 mM phosphate buffer |
| 7.5 | 100 mM phosphate buffer |
| 8.0 | 100 mM phosphate buffer |
| 8.5 | 10 mM borate buffer |

Example 1 was carried out by the procedure described below.

(1) The anti-tacrolimus solid phase antibody 1, the anti-tacrolimus solid phase antibody 2, and the anti-tacrolimus solid phase antibody 3 were diluted with PBS so as to make the concentration of each to 3 μg/mL; and then, the resulting solution was added to the 96 well immunoplate with the amount thereof of 50 μL per one well each, which was then followed by the reaction at 37° C. for 1 hour.

(2) The wells were washed with the washing solution for three times.

(3) The blocking solution was added with the amount thereof of 150 μL per one well each, which was then followed by the reaction at 4° C. for one overnight.

(4) The wells were washed with the washing solution for three times.

(5) The specimen was diluted with 10 times its volume of the acidic buffer; and then, the resulting solution was added with the amount thereof of 50 μL per one well each, which was then followed by the reaction at 37° C. for 10 minutes.

(6) The wells were washed with the washing solution for three times.

(7) The culture supernatant containing the anti-tacrolimus antibody was diluted with the diluted solution for the culture supernatant so as to make the concentration thereof to 0.2 μg/mL; and then, the resulting solution was added with the amount thereof of 50 μL per one well each, which was then followed by the reaction at 37° C. for 10 minutes.

(8) The wells were washed with the washing solution for three times.

(9) The ALP-labelled antibody was diluted with the diluted solution for the labelled antibody so as to make the concentration thereof to 0.1 μg/mL; and then, the resulting solution was added with the amount thereof of 50 μL per one well each, which was then followed by the reaction at 37° C. for 10 minutes.

(10) The wells were washed with the washing solution for three times.

(11) The luminescent substrate was added with the amount thereof of 50 μL per one well each, which was then followed by the reaction at room temperature for 5 minutes; and then, the luminescence was detected.

Figures 1, 2:
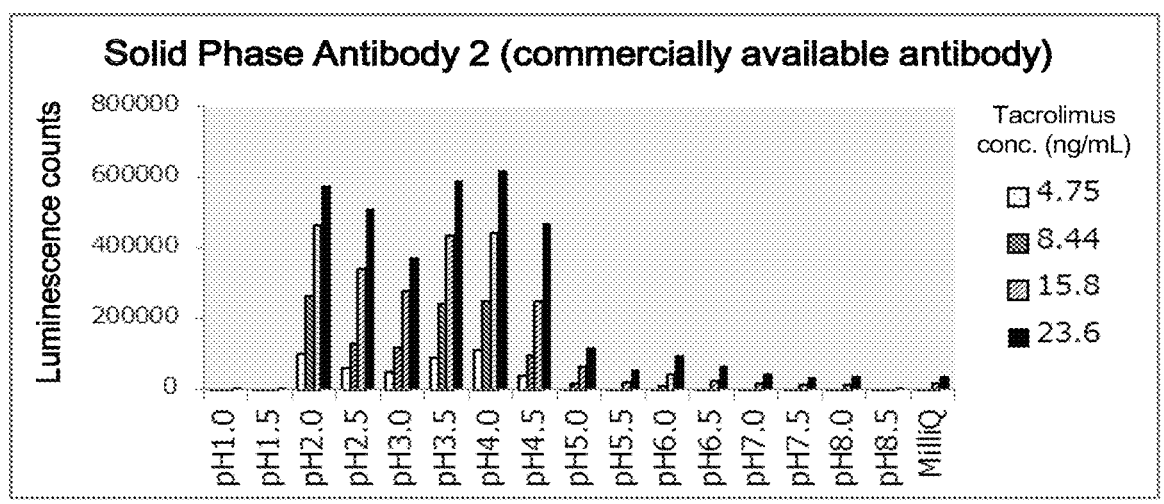
Figures 1, 2, 3:
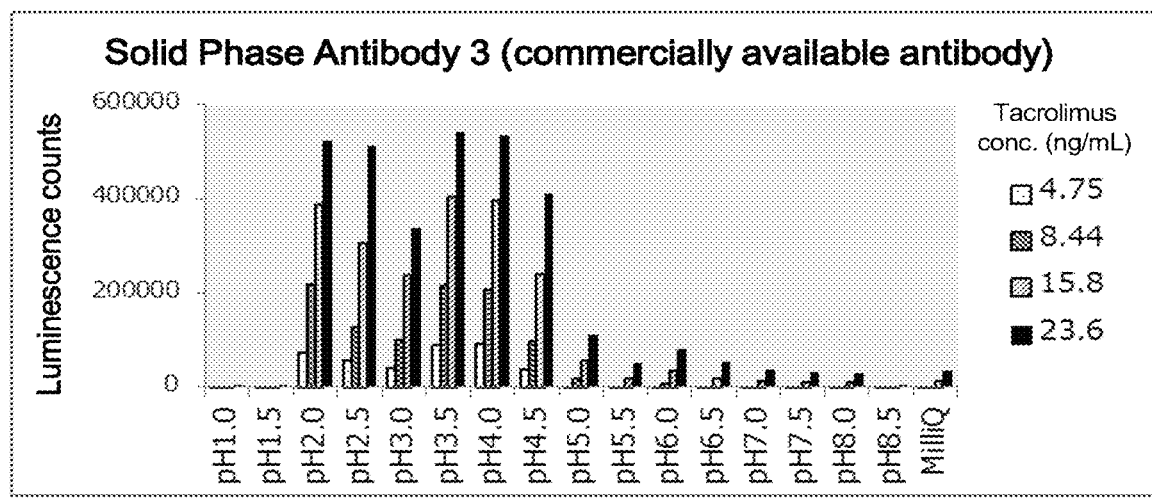
Figure 2:
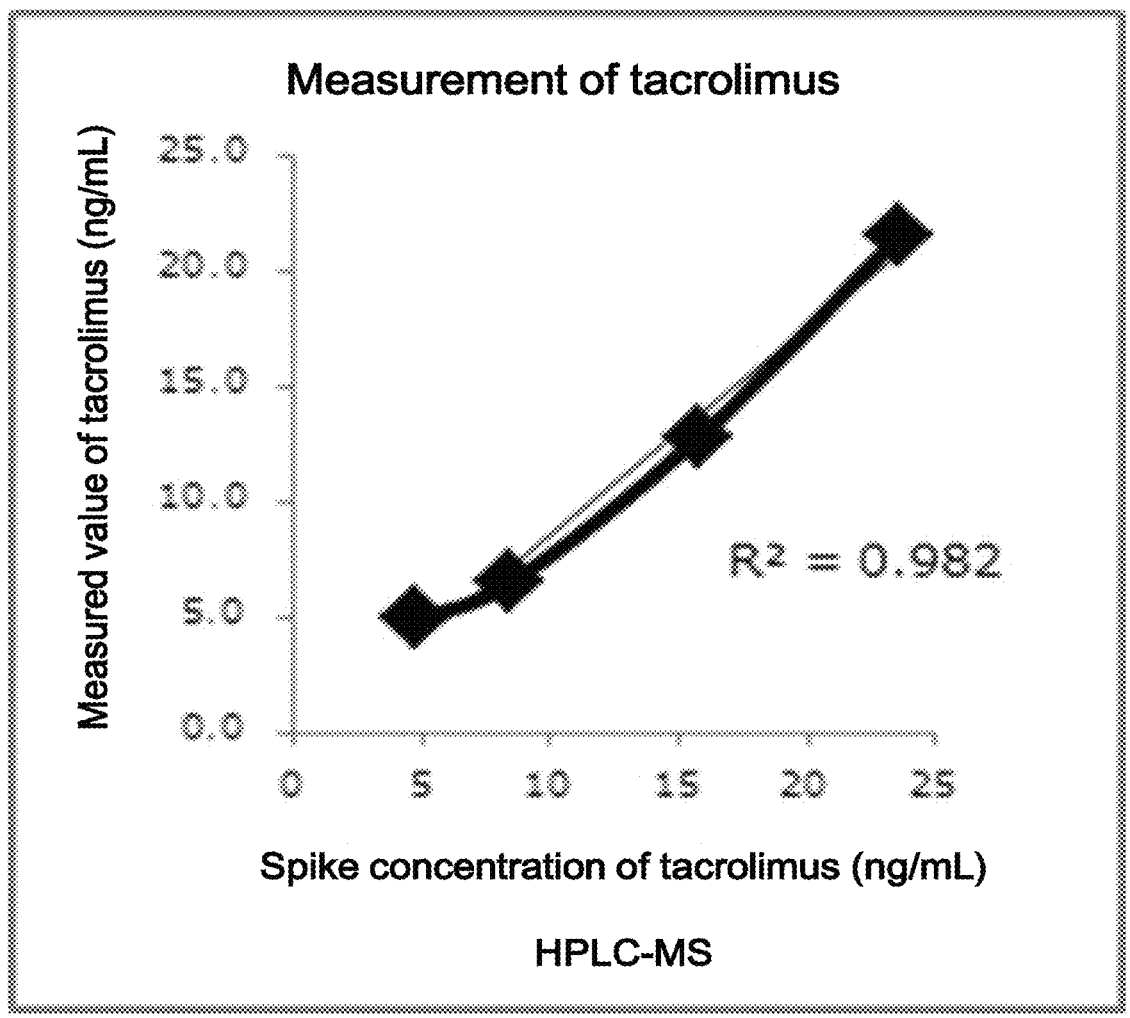
Figure 3:
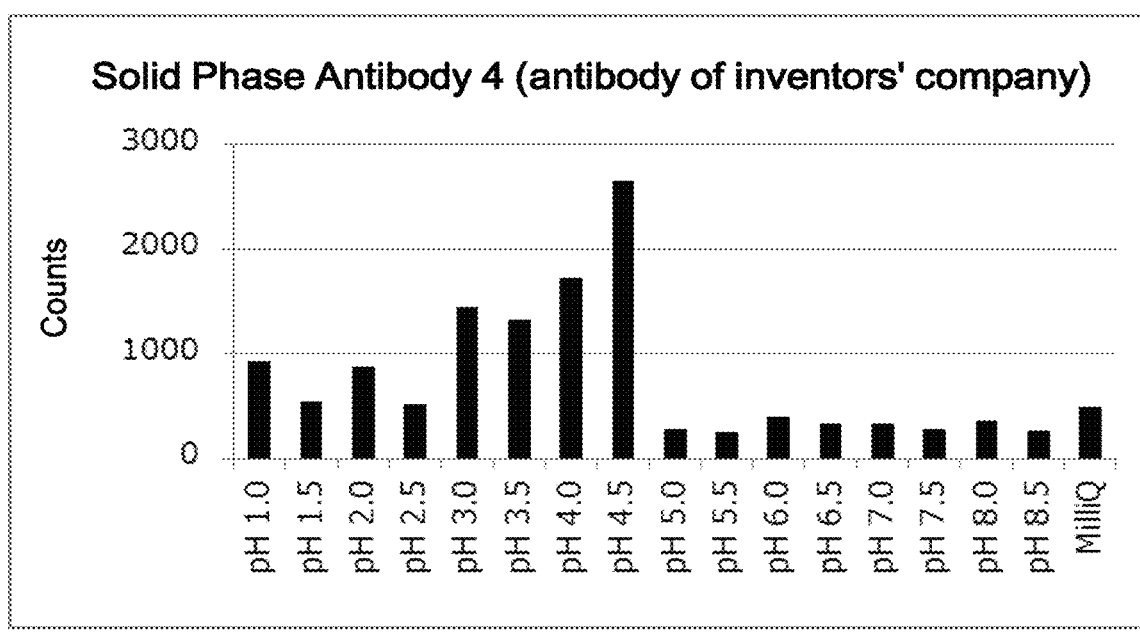

As a result, commonly in the experiments using 3 antibodies, the luminescence counts were observed in the acidic pH region according to tacrolimus concentration (FIG. 1-1 to FIG. 1-3). This indicates that in the acidic pH region, with dissociating tacrolimus from the specific binding proteins thereof (FKBP) and from non-specific binding proteins (albumin and so forth), the dissociated tacrolimus can be detected with the antibody.

Accordingly, it was demonstrated that pretreatment of the blood sample with an acid is effective when tacrolimus is detected with an antibody in the blood sample containing tacrolimus and the specific binding protein thereof.

Example 2: ELISA of Quantifying Tacrolimus in Whole Blood Specimen by Acid Treatment The materials used in Example 2 are as follows.
Acidic buffer: 100 mM phosphate buffer/pH 2.0
Substance for calibration curve: tacrolimus (1 mg/mL in DMSO)
Diluted solution for calibration curve: 0.5% Tween®20/PBS
Other materials used in Example 2 are the same as those used in Example 1.

Example 2 was carried out by the procedure described below.

(1) The anti-tacrolimus solid phase antibody 1 was diluted with PBS so as to make the concentration thereof to 3 μg/mL; and then, the resulting solution was added to the 96 well immunoplate with the amount thereof of 50 μL per one well each, which was then followed by the reaction at 37° C. for 1 hour.

(2) The wells were washed with the washing solution for three times.

(3) The blocking solution was added with the amount thereof of 150 μL per one well each, which was then followed by the reaction at 4° C. for one overnight.

(4) The wells were washed with the washing solution for three times.

(5A) The specimen was diluted with 10 times its volume of the phosphate buffer (pH 2.0); and then, the resulting solution was added with the amount thereof of 50 μL per one well each, which was then followed by the reaction at 37° C. for 10 minutes.

(5B) Tacrolimus (1 mg/mL in DMSO), the substance for a calibration curve, was diluted with the diluted solution for a calibration curve so as to give the dilution series of 40, 13, 4.4, 1.5, 0.49, 0.16, 0.050, and 0 ng/mL; and then, the resulting solution was added with the amount thereof of 50 μL per one well each, which was then followed by the reaction at 37° C. for 10 minutes.

(6) The wells were washed with the washing solution for three times.

(7) The culture supernatant containing the anti-tacrolimus antibody was diluted with the diluted solution for the culture supernatant so as to make the concentration thereof to 0.2 μg/mL; and then, the resulting solution was added with the amount thereof of 50 μL per one well each, which was then followed by the reaction at 37° C. for 10 minutes.

(8) The wells were washed with the washing solution for three times.

(9) The ALP-labelled antibody was diluted with the diluted solution for the labelled antibody so as to make the concentration thereof to 0.1 μg/mL; and then, the resulting solution was added with the amount thereof of 50 μL per one well each, which was then followed by the reaction at 37° C. for 10 minutes.

(10) The wells were washed with the washing solution for three times.

(11) The luminescent substrate was added with the amount thereof of 50 μL per one well each, which was then followed by the reaction at room temperature for 5 minutes; and then, the luminescence was detected.

(12) By using the linear approximation formula of the calibration curve, the tacrolimus measurement value was calculated on the basis of the count at the time of the specimen measurement.

As a result, when the blood sample containing tacrolimus, the specific binding proteins thereof, and non-specific binding proteins was pretreated with the acid, the measured value of the tacrolimus concentration exhibited a very high correlation with the spike concentration of tacrolimus (FIG. 2).

Accordingly, when the blood sample containing tacrolimus, the specific binding proteins thereof, and non-specific binding proteins was pretreated with the acid, it was demonstrated that the pretreatment is superior in the quantitativity of tacrolimus in the blood sample.

Example 3: ELISA of Detecting Cyclosporine A in Whole Blood Specimen by Acid Treatment The materials used in Example 3 are as follows.
Anti-cyclosporine solid phase antibody 1 (mouse IgG): CS5-12-27 (antibody of the inventors' company)
Acidic buffer: 10 mM acetate buffer/pH 4.0 Culture supernatant containing the anti-cyclosporine antibody: CHO culture supernatant containing anti-cyclosporine chicken IgM (antibody of the inventors' company)
Other materials used in Example 3 are the same as those used in Examples 1 and 2.

Example 3 was carried out by the procedure described below.

(1) The anti-cyclosporine solid phase antibody 1 was diluted with PBS so as to make the concentration thereof to 2.5 μg/mL; and then, the resulting solution was added to the 96 well immunoplate with the amount thereof of 50 μL per one well each, which was then followed by the reaction at 37° C. for 1 hour.

(2) The wells were washed with the washing solution for three times.

(3) The blocking solution was added with the amount thereof of 150 μL per one well each, which was then followed by the reaction at 4° C. for one overnight.

(4) The wells were washed with the washing solution for three times.

(5) The specimen was diluted with 10 times its volume of the acidic buffer; and then, the resulting was added with the amount thereof of 50 µL per one well each, which was then followed by the reaction at 37° C. for 10 minutes.

(6) The wells were washed with the washing solution for three times.

(7) The culture supernatant containing the anti-cyclosporine antibody was diluted with the diluted solution for the culture supernatant so as to make the concentration thereof to 0.2 µg/mL; and then, the resulting solution was added with the amount thereof of 50 µL per one well each, which was then followed by the reaction at 37° C. for 10 minutes.

(8) The wells were washed with the washing solution for three times.

(9) The ALP-labelled antibody was diluted with the diluted solution for the labelled antibody so as to make the concentration thereof to 0.1 µg/mL; and then, the resulting solution was added with the amount thereof of 50 µL per one well each, which was then followed by the reaction at 37° C. for 10 minutes.

(10) The wells were washed with the washing solution for three times.

(11) The luminescent substrate was added with the amount thereof of 50 µL per one well each, which was then followed by the reaction at room temperature for 5 minutes; and then, the luminescence was detected.

As a result, in the experiment using the antibody, high luminescence counts were recognized in the acidic pH region (FIG. 3). This indicates that in the acidic pH region, with dissociating cyclosporine A from the specific binding proteins thereof (cyclophilin) and from non-specific binding proteins (albumin and so forth), the cyclosporine A thus dissociated can be detected with the antibody.

Accordingly, it was demonstrated that pretreatment of the blood sample with an acid is effective in the detection of cyclosporine A in the blood sample containing cyclosporine A and the specific binding protein thereof.

Example 4: ELISA of Quantifying Cyclosporine A in Whole Blood Specimen by Acid Treatment The materials used in Example 4 are as follows.
Acidic buffer: 10 mM acetate buffer/pH 4.0
Substance for calibration curve: cyclosporine A (1 mg/mL in DMSO)
Diluted solution for calibration curve: 0.5% Tween®20/PBS Other materials used in Example 4 are the same as those used in Examples 1 to 3.

Example 4 was carried out by the procedure described below.

(1) The anti-cyclosporine solid phase antibody 1 was diluted with PBS so as to make the concentration thereof to 2.5 µg/mL; and then, the resulting solution was added to the 96 well immunoplate with the amount thereof of 50 µL per one well each, which was then followed by the reaction at 37° C. for 1 hour.

(2) The wells were washed with the washing solution for three times.

(3) The blocking solution was added with the amount thereof of 150 µL per one well each, which was then followed by the reaction at 4° C. for one overnight.

(4) The wells were washed with the washing solution for three times.

(5A) The specimen was diluted with 10 times its volume of the acetate buffer (pH 4.0); and then, the resulting solution was added with the amount thereof of 50 µL per one well each, which was then followed by the reaction at 37° C. for 10 minutes.

(5B) Cyclosporine A (1 mg/mL in DMSO) was diluted with the diluted solution for a calibration curve so as to give the dilution series of 200, 100, 50.0, 25.0, 12.5, 6.25, 3.13, and 0 ng/mL; and then, the resulting solution was added with the amount thereof of 50 µL per one well each, which was then followed by the reaction at 37° C. for 10 minutes.

(6) The wells were washed with the washing solution for three times.

(7) The culture supernatant containing the anti-cyclosporine antibody was diluted with the diluted solution for the culture supernatant so as to make the concentration thereof to 0.3 µg/mL; and then, the resulting solution was added with the amount thereof of 50 µL per one well each, which was then followed by the reaction at 37° C. for 10 minutes.

(8) The wells were washed with the washing solution for three times.

(9) The ALP-labelled antibody was diluted with the diluted solution for the labelled antibody so as to make the concentration thereof to 0.1 µg/mL; and then, the resulting solution was added with the amount thereof of 50 µL per one well each, which was then followed by the reaction at 37° C. for 10 minutes.

(10) The wells were washed with the washing solution for three times.

(11) The luminescent substrate was added with the amount thereof of 50 µL per one well each, which was then followed by the reaction at room temperature for 5 minutes; and then, the luminescence was detected.

(12) By using the linear approximation formula of the calibration curve, the cyclosporine A measurement value was calculated on the basis of the count at the time of the specimen measurement.

Figure 4:
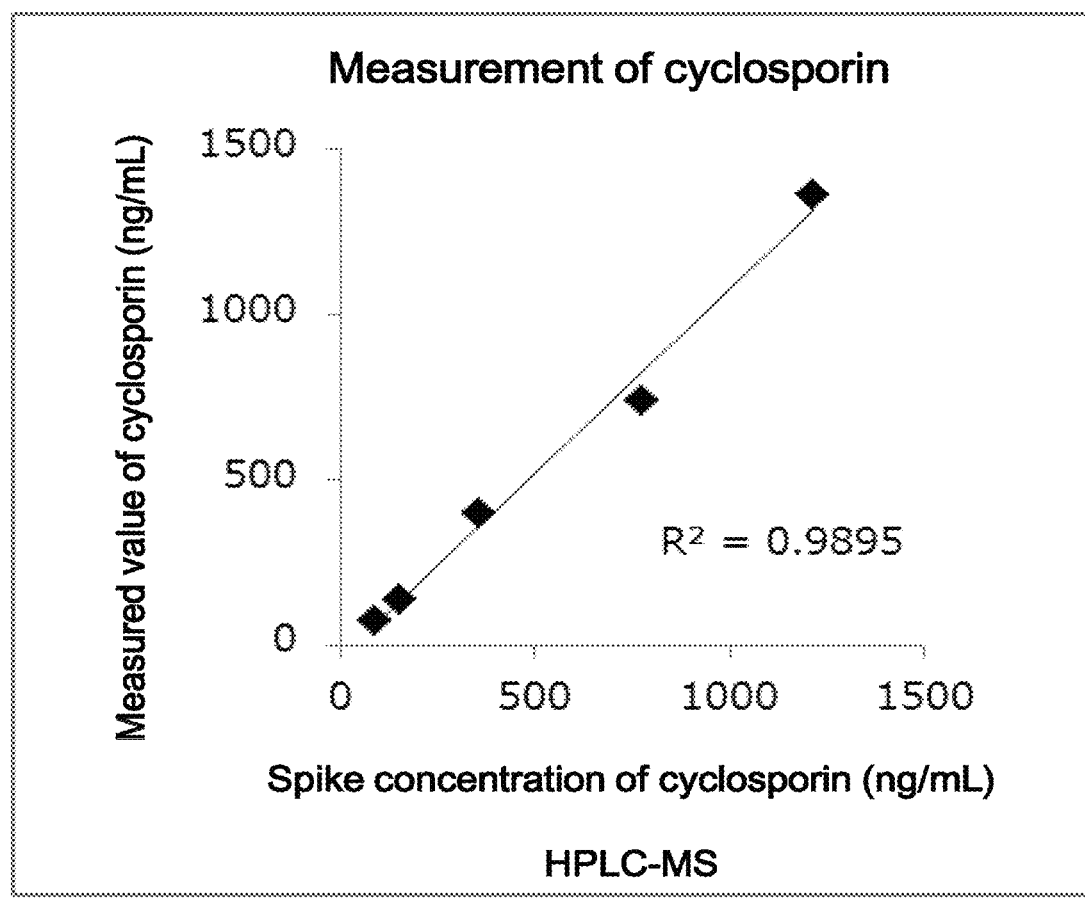
FIG. 4 illustrates the correlation between the measured value of the cyclosporine A concentration and the spike concentration of cyclosporine A in the specimen when the blood sample containing cyclosporine A (substance for calibration curve) and the binding protein thereof is pretreated with an acid.

As a result, when the blood sample containing cyclosporine A, the specific binding proteins thereof, and non-specific binding proteins was pretreated with the acid, the measured value of cyclosporine A concentration exhibited a very high correlation with the spike concentration of cyclosporine A (FIG. 4).

Accordingly, when the blood sample containing cyclosporine A, the specific binding proteins thereof, and non-specific binding proteins was pretreated with the acid, it was demonstrated that the pretreatment is superior in the quantitativity of cyclosporine A in the blood sample.

Example 5: Confirmation of Effect to Specificity of Solid Phase Antibody in Measurement in Acidic Solution Materials used in Example 5 are as follows.
Surfactant-containing acidic buffer: 0.5% Tween®20/10 mM acetate buffer/pH 4.0
Surfactant-containing neutral buffer: 0.5% Tween®20/PBS/pH 6.8
Biotin-labelled tacrolimus: Tac-PEG2-Biotin (1 mg/mL in DMSO, prepared in the inventors' company)
Tacrolimus analogous compound 1: sirolimus
Tacrolimus analogous compound 2: everolimus
Tacrolimus analogous compound 3: temsirolimus
Tacrolimus analogous compound 4: pimecrolimus
Tacrolimus analogous compound 5: dihydro FK506
Tacrolimus: tacrolimus (1 mg/mL in DMSO)
ALP-labelled streptavidin: alkaline phosphatase-labelled streptavidin (Calbiochem)

Diluted solution: 1% by weight BSA/TBS

Other materials used in Example 5 are the same as those used in Examples 1 to 4.

Example 5 was carried out by the procedure described below.

(A) Preparation of a Mixed Solution of the Biotin-Labelled Tacrolimus and the Tacrolimus Analogous Compound
  (1) The biotin-labeled tacrolimus was diluted with the surfactant-containing acidic buffer or with the surfactant-containing neutral buffer so as to make the concentration thereof to 10 ng/mL.
  (2) Tacrolimus or the tacrolimus analogous compound (1 mg/mL in DMSO) was added to the solution containing the biotin-labelled tacrolimus prepared in (1) to prepare the dilution series diluted from 100,000 ng/mL by 10 times each as the final concentration.

(B) Inhibition Assay
  (1) The anti-tacrolimus solid phase antibody 1 was diluted with PBS so as to make the concentration thereof to 3 µg/mL; and then, the resulting solution was added to the 96 well immunoplate with the amount thereof of 50 µl, per one well each, which was then followed by the reaction at 37° C. for 1 hour.
  (2) The wells were washed with the washing solution for three times.
  (3) The blocking solution was added with the amount thereof of 150 µL per one well each, which was then followed by the reaction at 4° C. for one overnight.
  (4) The wells were washed with the washing solution for three times.
  (5) The mixed solution of the biotin-labelled tacrolimus and the tacrolimus analogous compound prepared in (A) was added with the amount thereof of 50 µL per one well each, which was then followed by the reaction at 37° C. for 1 hour.
  (6) The wells were washed with the washing solution for three times.
  (7) The ALP-labelled streptavidin was diluted with the diluted solution so as to make the concentration thereof to 0.1 µg/mL; and then, the resulting solution was added with the amount thereof of 50 µL per one well each, which was then followed by the reaction at 37° C. for 10 minutes.
  (8) The wells were washed with the washing solution for three times.
  (9) The luminescent substrate was added with the amount thereof of 50 µL per one well each, which was then followed by the reaction at room temperature for 5 minutes; and then, the luminescence was detected.

Figures 1, 5:
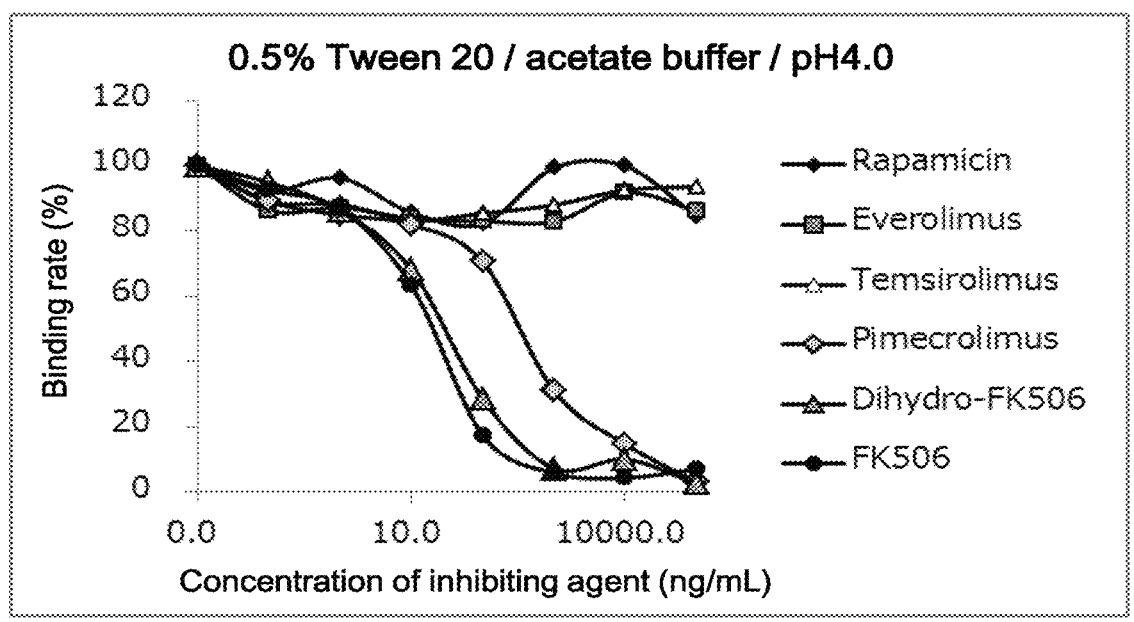
Figures 2, 5:
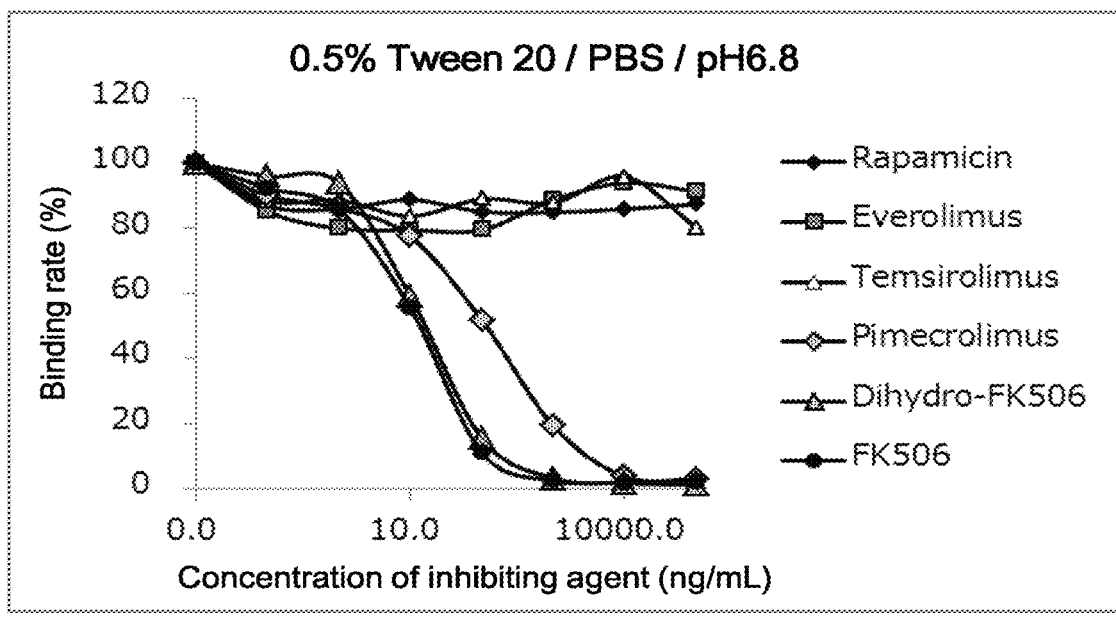

As a result, in the inhibition experiment using the anti-tacrolimus solid phase antibody and the biotin-labelled tacrolimus, and various tacrolimus analogous compounds, which are agents of inhibiting binding thereof, the binding inhibiting type in the acetic solution was the same as that in the neutral solution (FIG. 5-1 and FIG. 5-2). This indicates that the acidic condition does not affect specificity of the antibody.

Accordingly, it was demonstrated that specificity of the antibody was maintained in the acidic solution.

Example 6: Confirmation of Dissociation of Macrolide Immunosuppressant from Specific Binding Protein in Acid Treatment Materials used in Example 6 are as hollows.
FKBP12: recombinant FKBP12 (Sino Biological Inc., catalogue No.: 10268-H08E)
Tacrolimus: tacrolimus (Img/mL in DMSO)
Tacrolimus·FKBP diluted solution 1: 0.5% Tween®20/PBS
Tacrolimus·FKBP diluted solution 2: 0.5% Tween®20/200 mM phosphate buffer/pH 2.0

Other materials used in Example 6 are the same as those used in Examples 1 to 5.

Example 6 was carried out by the procedure described below.

(A) Binding of Tacrolimus with FKBP12
  (1) Tacrolimus was diluted with the tacrolimus·FKBP diluted solution 1 so as to give the dilution series of 240 ng/mL, 80 ng/mL, 26.6 ng/mL, 8.89 ng/mL, 1.48 ng/mL, 0.49 ng/mL, 0.165 ng/mL, and 0 ng/mL.
  (2) FKBP12 was diluted with the tacrolimus·FKBP diluted solution 1 so as to make the concentration thereof to 100 µg/mL.
  (3) The same amounts of the diluted tacrolimus and the diluted FKBP 12 were mixed (for example, final concentration: tacrolimus 120 µg/mL+FKBP12 50 µg/mL, tacrolimus 40 µg/mL+FKBP12 50 µg/mL, etc.).
  (4) Tacrolimus and FKBP12 were reacted in the solution at room temperature for 1 hour.

(B) Dissociation Experiment of Bound Tacrolimus and FKBP12 Bound Each Other
  (1) The anti-tacrolimus solid phase antibody 1 was diluted with PBS so as to make the concentration thereof to 3 µg/mL; and then, the resulting solution was added to the 96 well immunoplate with the amount thereof of 50 µL per one well each, which was then followed by the reaction at 37° C. for 1 hour.
  (2) The wells were washed with the washing solution for three times.
  (3) The blocking solution was added with the amount thereof of 150 µL per one well each, which was then followed by the reaction at 4° C. for one overnight.
  (4) The wells were washed with the washing solution for three times.
  (5) The mixed solution of tacrolimus and FKBP12 prepared in (A) was diluted with 10 times its volume of the tacrolimus·FKBP diluted solution 1 or the tacrolimus·FKBP diluted solution 2; and then, the resulting solution was added with the amount thereof of 50 µL per one well each, which was then followed by the reaction at 37° C. for 10 minutes.
  (6) The wells were washed with the washing solution for three times.
  (7) The culture supernatant containing the anti-tacrolimus antibody was diluted with the diluted solution for the culture supernatant so as to make the concentration thereof to 0.2 µg/mL; and then, the resulting solution was added with the amount thereof of 50 µL per one well each, which was then followed by the reaction at 37° C. for 10 minutes.
  (8) The wells were washed with the washing solution for three times.
  (9) The ALP-labelled antibody was diluted with the diluted solution for the labelled antibody so as to make the concentration thereof to 0.1 µg/mL; and then, the resulting solution was added with the amount thereof of 50 µL per one well each, which was then followed by the reaction at 37° C. for 10 minutes.
  (10) The wells were washed with the washing solution for three times.
  (11) The luminescent substrate was added with the amount thereof of 50 µL per one well each, which was then followed by the reaction at room temperature for 5 minutes; and then, the luminescence was detected.

Figure 6:
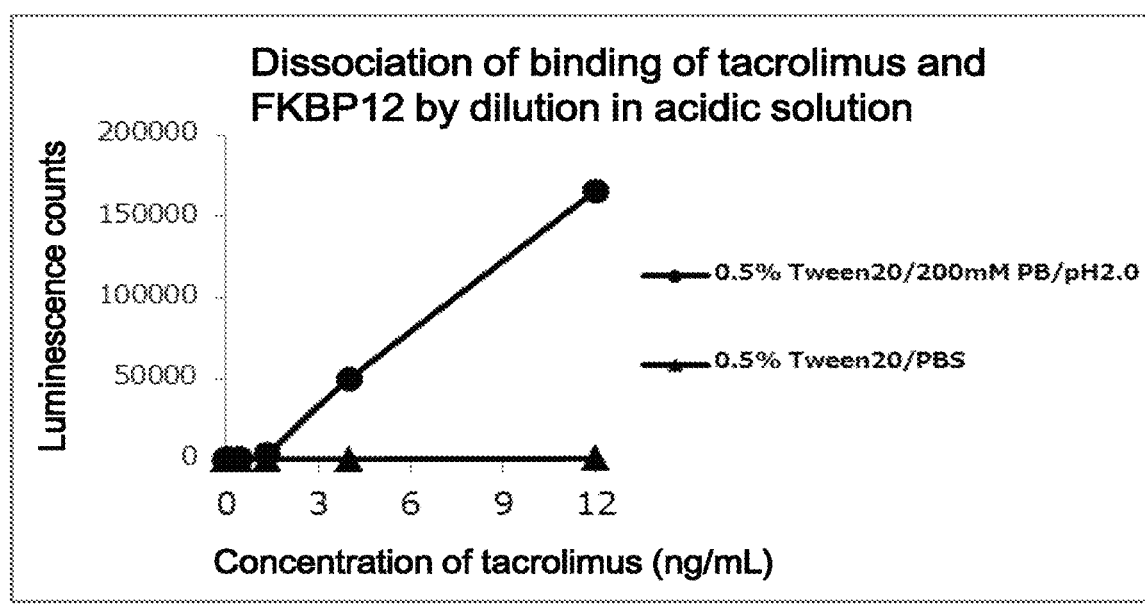
FIG. 6 illustrates compatibility between dissociation of the binding of tacrolimus with the specific binding protein thereof and binding of the dissociated tacrolimus with an antibody in the acidic solution.

As a result, when tacrolimus and FKBP12 were mixed followed by dilution of the resulting mixed solution with the neutral solution thereby effecting the antigen-antibody reaction under the neutral condition, signal that is depended on the tacrolimus concentration was not observed (under the condition of 0.5% Tween®20/200 mM PBS in FIG. 6). On the other hand, when tacrolimus and FKBP12 were mixed followed by dilution of the resulting mixture with the acidic solution thereby effecting the antigen-antibody reaction in the acidic solution, the signal that is depended on the tacrolimus concentration was observed (under the condition of 0.5% Tween®20/200 mM PB/pH 2.0 in FIG. 6). This indicates that under the acidic condition, with dissociating the binding between tacrolimus and FKBP12, concentration of the dissociated tacrolimus can be measured with the antibody.

Considering the results of this Example together with the results of Examples 1 to 5, it was demonstrated that pretreatment of the blood sample with the acid is effective when concentration of the immunosuppressant in the blood sample containing the macrolide substance (the macrolide immunosuppressant or the metabolite thereof having the macrolide structure) and the specific binding protein thereof is measured with the antibody.

Example 7: ELISA of Detecting Tacrolimus in Whole Blood Specimen by Alkali Treatment The materials used in Example 7, such as the 96 well immunoplate, the anti-tacrolimus solid phase antibody 1, the washing solution, and the blocking solutions, are the same as those used in Examples 1 to 6.

Example 7 was carried out by the procedure described below.

(1) The anti-tacrolimus solid phase antibody 1 was diluted with PBS so as to make the concentration thereof to 3 µg/mL; and then, the resulting solution was added to the 96 well immunoplate with the amount thereof of 50 µL per one well each, which was then followed by the reaction at 37° C. for 1 hour.
(2) The wells were washed with the washing solution for three times.
(3) The blocking solution was added with the amount thereof of 150 µL per one well each, which was then followed by the reaction at 4° C. for one overnight.
(4) The wells were washed with the washing solution for three times.
(5) Each of four specimens whose tacrolimus concentrations had been known was diluted with 10 times its volume of the neutral buffer (50 mM phosphate buffer: pH 7.0) or with the basic buffer (50 mM MES: pH 10.0); and then, the resulting solution was added with the amount thereof of 50 µL per one well each, which was then followed by the reaction at 37° C. for 10 minutes.
(6) The wells were washed with the washing solution for three times.
(7) The anti-tacrolimus IgM antibody was diluted with the diluted solution for the anti-tacrolimus IgM antibody so as to make the concentration thereof to 0.5 µg/mL; and then, the resulting solution was added with the amount thereof of 50 µL per one well each, which was then followed by the reaction at 37° C. for 10 minutes.
(8) The wells were washed with the washing solution for three times.
(9) The alkaline phosphatase-labelled anti-chicken IgM antibody was diluted with the diluted solution for the labelled antibody so as to make the concentration thereof to 0.1 µg/mL; and then, the resulting solution was added with the amount thereof of 50 µL per one well each, which was then followed by the reaction at 37° C. for 10 minutes.
(10) The wells were washed with the washing solution for three times.
(11) The luminescent substrate was added with the amount thereof of 50 µL per one well each, which was then followed by the reaction at room temperature for 5 minutes; and then, the luminescence was detected.

Figure 7:
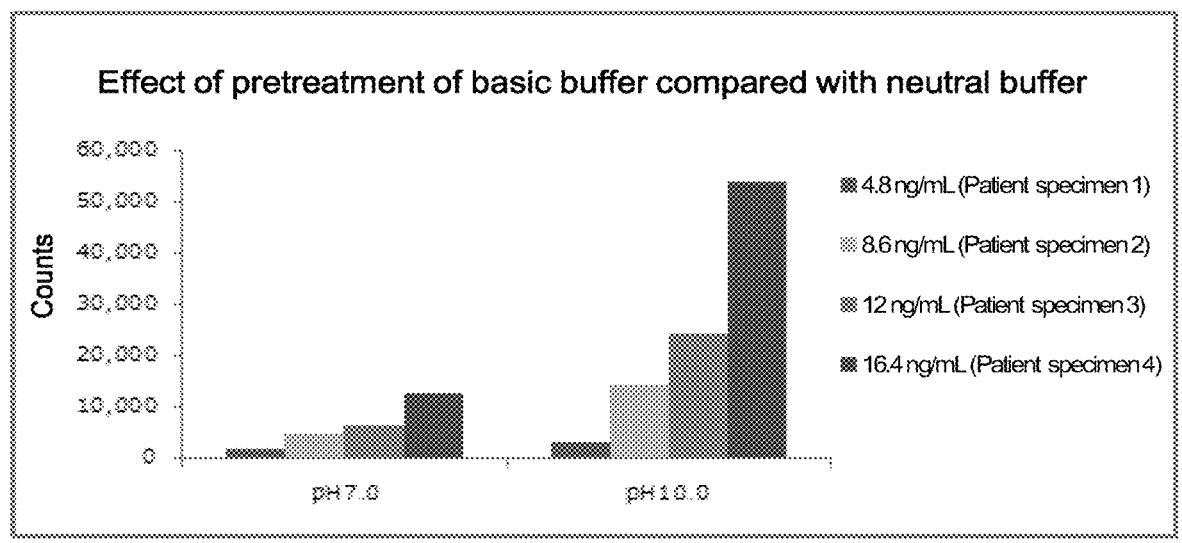
FIG. 7 illustrates the immunoassay result of tacrolimus that is dissociated from the tacrolimus-bound protein when the alkaline solution is used for pretreatment of the whole blood specimen (solid phase antibody: anti-tacrolimus antibody (mouse IgG: antibody of the inventors' company); detection antibody: anti-tacrolimus chicken IgM).

The results of the luminescent counts under these conditions are illustrated in FIG. 7. In the case that the whole blood specimen was treated by mixing with the alkaline buffer, the obtained luminescent count was detected dependent on the tacrolimus concentration, and was detected higher as compared with the case that it was mixed with the neutral buffer.

Accordingly, it was demonstrated that when the blood sample containing tacrolimus was pretreated with the alkali, tacrolimus in this blood sample could be measured with a high sensitivity.

Example 8: ELISA of Detecting Tacrolimus in Whole Blood Specimen by Acid Treatment and Neutralization Treatment Materials used in Example 8 are as follows.
Acidic buffer: 50 mM phosphate buffer/pH 2.0
Neutral buffer: 200 mM phosphate buffer/pH 7.0
Neutralization solution 1: 8 M urea/200 mM phosphate buffer/pH 8.0
Neutralization solution 2: 4 M guanidine hydrochloride salt/200 mM phosphate buffer/pH 8.0
Other materials used in Example 8 are the same as those used in Examples 1 to 7.

Example 8 was carried out by the procedure described below.

(1) The anti-tacrolimus solid phase antibody 1 was diluted with PBS so as to make the concentration thereof to 3 µg/mL; and then, the resulting solution was added to the 96 well immunoplate with the amount thereof of 50 µL per one well each, which was then followed by the reaction at 37° C. for 1 hour.
(2) The wells were washed with the washing solution for three times.
(3) The blocking solution was added with the amount thereof of 150 µL per one well each, which was then followed by the reaction at 4° C. for one overnight.
(4) The wells were washed with the washing solution for three times.
(5) After 24 µL of the acidic buffer was added to 6 µL of the specimen to cause the reaction therebetween, the specimen thus pretreated was neutralized by adding 30 µL of the neutralization solution 1 or of the neutralization solution 2. For comparison, after the specimen was diluted with 5 times its volume of the neutral buffer, it was diluted with two times its volume of the neutral buffer (pH 7.0) containing 8 M urea or 4 M guanidine hydrochloride salt, and diluted with 10 times its volume of the neutral buffer, thereby obtaining the samples.
(6) The treated sample was added with the amount thereof of 50 µL per one well each, which was then followed by the reaction at 37° C. for 10 minutes.

(7) The wells were washed with the washing solution for three times.
(8) The anti-tacrolimus IgM antibody was diluted with the diluted solution for the anti-tacrolimus IgM antibody so as to make the concentration thereof to 0.5 µg/mL; and then, the resulting solution was added with the amount thereof of 50 µL per one well each, which was then followed by the reaction at 37° C. for 10 minutes.
(9) The wells were washed with the washing solution for three times.
(10) The alkaline phosphatase-labelled anti-chicken IgM antibody was diluted with the diluted solution for the labelled antibody so as to make the concentration thereof to 0.1 µg/mL; and then, the resulting solution was added with the amount thereof of 50 µL per one well each, which was then followed by the reaction at 37° C. for 10 minutes.
(11) The wells were washed with the washing solution for three times.
(12) The luminescent substrate was added with the amount thereof of 50 µL per one well each, which was then followed by the reaction at room temperature for 5 minutes; and then, the luminescence was detected.

Figures 1, 8:
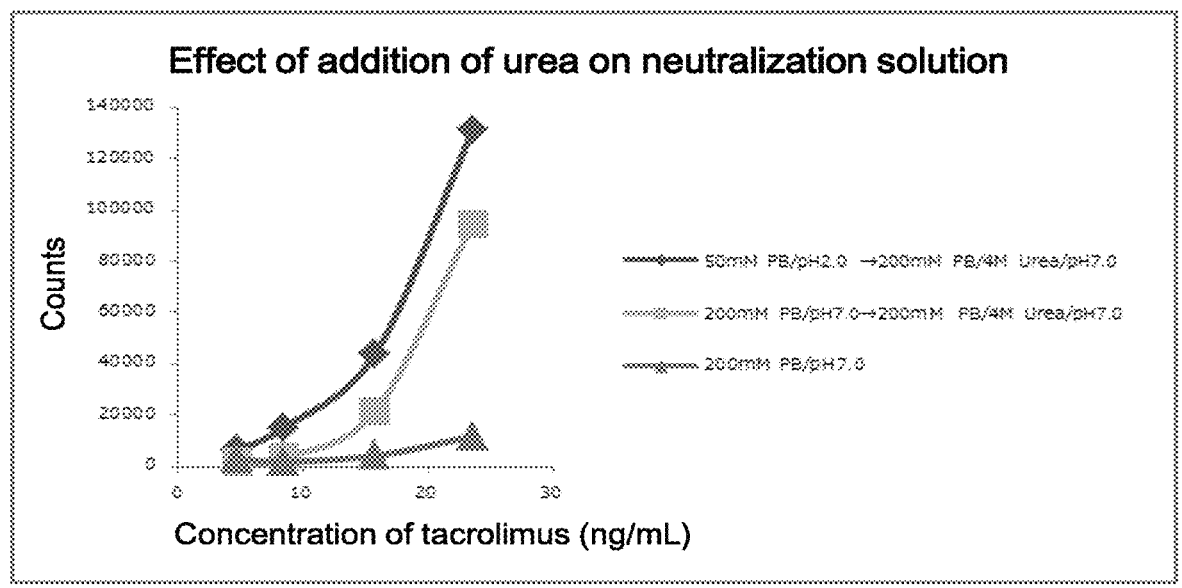
Figures 2, 8:
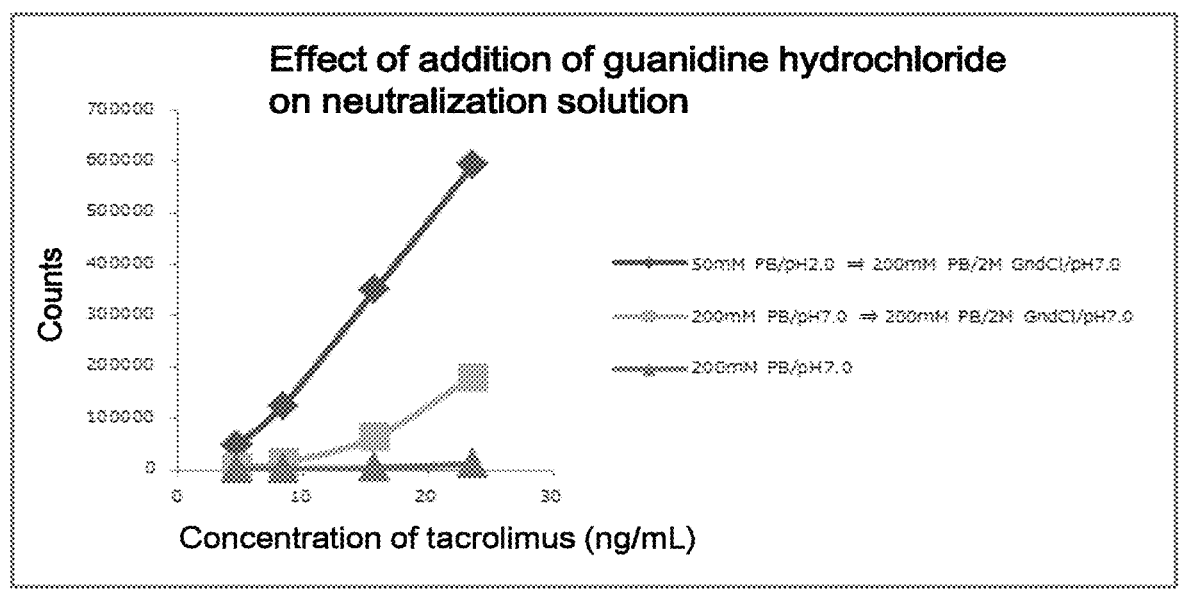

Results of the luminescent counts under each condition are described in FIG. 8. when the specimen was subjected to the acid treatment, and then this specimen was neutralized by the neutralization solution containing the chaotropic denaturing agent (especially, guanidine hydrochloride), it was observed that the counts were significantly increased as compared with the case that it was diluted only with the neutral buffer. On the other hand, in the case that only the chaotropic denaturing agent was added without the acid treatment, it was observed that the counts were also increased.

Example 9: ELISA of Detecting Everolimus in Whole Blood Specimen by Acid Treatment and Neutralization Treatment Materials used in Example 9 are as follows.
Conjugate solid phase: everolimus-BSA conjugate (antibody of the inventors' company)
Anti-everolimus antibody (rabbit polyclonal antibody): EVER antibody solution 1 (everolimus kit Nanopia TDM everolimus, manufactured by Sekisui Medical Co., Ltd.)
Washing solution: lumipulse washing solution
Specimen: ClinCal (registered trade mark) Whole Blood Calibrator Set Lyophilised (RECIPE). The measured values of everolimus by HPLC-MS used in the present invention are 0 ng/ml (level 0), 1.45 ng/ml (level 1), 2.86 ng/ml (level 2), 5.27 ng/ml (level 3), 11.7 ng/ml (level 4), 23.2 ng/mL (level 5), and 48.0 ng/ml (level 6).
ALP-labelled antibody: alkaline phosphatase-labelled pig anti-rabbit Ig polyclonal antibody (DAKO, catalogue No. D0306)
Antibody diluted solution: 0.5% by volume Tween®20/PBS
Other materials used in Example 9 are the same as those in Examples 1 to 8.
Example 9 was carried out by the procedure described below.
(1) The everolimus-BSA conjugate was diluted with PBS so as to make the concentration thereof to 5 µg/mL; and then, the resulting solution was added to the 96 well immunoplate with the amount thereof of 50 µL per one well each, which was then followed by the reaction at 37° C. for 1 hour.
(2) The wells were washed with the washing solution for three times.
(3) The blocking solution was added with the amount thereof of 150 µL per one well each, which was then followed by the reaction at 4° C. for one overnight.
(4) The wells were washed with the washing solution for three times.
(5) After 6 µL of the specimen was caused to react with 48 µL of the acidic buffer, this was added with 18 µL of the neutralization solution 2 or of the acidic buffer to obtain the pretreated solution. This pretreated solution and the antibody solution diluted to five times its volume were mixed at the volume ratio of 1:1; and then, the resulting solution was added to the 96 well immunoplate having the everolimus-BSA conjugate immobilized thereon, with the amount thereof of 50 µL per one well each, which was then followed by the reaction at 37° C. for 1 hour.
(6) The wells were washed with the washing solution for three times.
(7) The ALP-labelled antibody was diluted with the antibody diluted solution so as to make the concentration thereof to 0.2 µg/mL; and then, the resulting solution was added with the amount thereof of 50 µL per one well each, which was then followed by the reaction at 37° C. for 10 minutes.
(8) The wells were washed with the washing solution for three times.
(9) The luminescent substrate was added with the amount thereof of 50 µL per one well each, which was then followed by the reaction at room temperature for 5 minutes; and then, the luminescence was detected.

Figure 9:
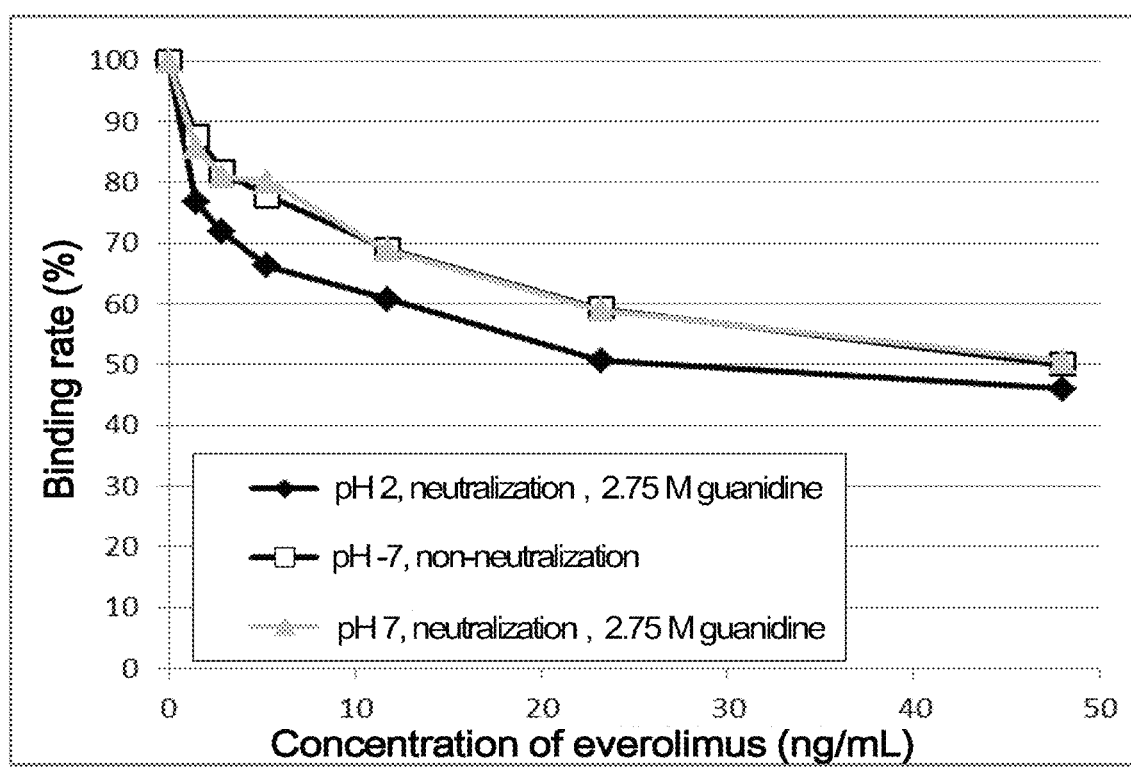
FIG. 9 illustrates the binding rate (%) of the anti-everolimus antibody with the everolimus-BSA conjugate in accordance with the everolimus concentration in the specimen that is obtained by treating the whole blood specimen with the neutralization solution containing guanidine hydrochloride salt after treating this whole blood specimen with an acid.

Results of the luminescent counts under these conditions are described in FIG. 9. In the specimen not neutralized after subjecting the whole blood specimen to the acid treatment, the luminescent count could not be obtained (data are not illustrated) probably because the anti-everolimus antibody might be deactivated by the acid. In the pretreated solution that had been neutralized with the guanidine-containing neutralization solution after treating the whole blood specimen with the acidic buffer of pH 2.0, everolimus could be detected with higher sensitivity than the specimen added with the neutral buffer in place of the acidic buffer. This indicates that the acidic buffer can effectively extract everolimus from the whole blood specimen.

Accordingly, it was demonstrated that when everolimus in the blood sample containing everolimus and the specific binding protein thereof is detected with the antibody, pretreatment of the blood sample with the acid is effective. In addition, it was demonstrated that in the case that the antibody whose resistance to an acid is low is used, when the specimen was subjected to the neutralization treatment after the acid treatment and before the antigen-antibody reaction, everolimus could be efficiently detected.

INDUSTRIAL APPLICABILITY

The present invention is useful, for example, for Therapeutic Drug Monitoring (TDM) of the macrolide immunosuppressant.

The invention claimed is:
1. A method of testing a blood for a macrolide immunosuppressant that is tacrolimus, the method comprising:

(a) treating a blood sample comprising tacrolimus with an acidic buffer having a pH in a range of 2.0 to 4.5 to form an acidic blood sample containing the tacrolimus, and wherein the acidic blood sample containing the tacrolimus does not contain a volatile organic solvent; and
(b) measuring a concentration of the tacrolimus in the acidic blood sample by contacting the acidic blood sample with an antibody that specifically binds to the tacrolimus, and the antibody is IgG, IgM, or an antibody fragment thereof, and immobilized to a solid phase.

2. The method of claim 1, wherein the blood sample is a human blood sample.

* * * * *